United States Patent [19]
Schreck et al.

[11] 4,374,055
[45] Feb. 15, 1983

[54] ALKYL ESTERS OF 1-ALKANOYL CYCLOALKANOLS AND ORGANOLEPTIC USES THEREOF

[75] Inventors: Ronald P. Schreck, Old Bridge, N.J.; Kenneth K. Light, North Ogden, Utah; John B. Hall, Rumson, N.J.; Frederick L. Schmitt, Holmdel, N.J.; Manfred H. Vock, Locust, N.J.; William L. Schreiber, Jackson, N.J.; Joaquin F. Vinals, Red Bank, N.J.; Jacob Kiwala, Brooklyn, N.Y.

[73] Assignee: International Flavors & Fragrances Inc., New York, N.Y.

[21] Appl. No.: 314,002

[22] Filed: Oct. 22, 1981

Related U.S. Application Data

[62] Division of Ser. No. 133,828, Mar. 25, 1980, Pat. No. 4,327,749.

[51] Int. Cl.$^3$ .............................................. A61K 7/46
[52] U.S. Cl. ............................... 252/522 R; 426/536; 252/174.11
[58] Field of Search .................................. 252/522 R

[56] References Cited

FOREIGN PATENT DOCUMENTS 7605668 12/1976 Netherlands .................. 252/522 R

*Primary Examiner*—Thomas A. Waltz
*Attorney, Agent, or Firm*—Arthur L. Liberman

[57] ABSTRACT

Described is a process for preparing several substituted or unsubstituted cycloalkyl acyl alkanoates defined according to the generic structure:

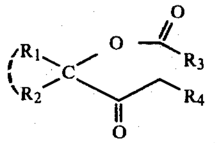

wherein $R_1$ and $R_2$ taken together complete a cycloalkyl moiety or methyl, dimethyl or trimethyl substituted cycloalkyl moiety containing five or six carbon atoms in the ring and wherein $R_3$ is $C_1$–$C_3$ lower alkyl and $R_4$ is methyl or hydrogen by reacting a compound having the generic structure:

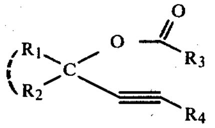

in an aqueous silver-ion containing solution having a weakly acidic pH at elevated temperatures. The compounds so produced are useful for their organoleptic properties in consumable materials, such as foodstuffs, foodstuff flavorants, chewing gums, chewing gum flavorants, toothpastes, toothpaste flavorants, medicinal products, medicinal product flavorants, chewing tobaccos, chewing tobacco flavorants, smoking tobaccos, smoking tobacco flavorants, perfume compositions, perfumed articles, such as cationic, anionic, nonionic and zwitterionic detergents, fabric softener compositions, drier-added fabric softener articles, textile sizing agents and optical brighteners for textiles as well as colognes.

2 Claims, 14 Drawing Figures

GLC PROFILE FOR EXAMPLE I

GLC PROFILE FOR EXAMPLE I.

MASS SPECTRUM FOR EXAMPLE I.

I R SPECTRUM FOR EXAMPLE III

GLC PROFILE FOR EXAMPLE II.

NMR SPECTRUM FOR EXAMPLE II.

I R SPECTRUM FOR EXAMPLE II.

GLC PROFILE FOR EXAMPLE III

NMR SPECTRUM FOR EXAMPLE III.

I R SPECTRUM FOR EXAMPLE III.

MASS SPECTRUM FOR EXAMPLE XXVIII (D).

NMR SPECTRUM FOR EXAMPLE XXVIII (D).

I R SPECTRUM FOR EXAMPLE XXVIII (D).

ALKYL ESTERS OF 1-ALKANOYL CYCLOALKANOLS AND ORGANOLEPTIC USES THEREOF

This is a division of application Ser. No. 133,828, filed Mar. 25, 1980, now U.S. Pat. No. 4,327,749.

BACKGROUND OF THE INVENTION

The present invention provides compounds having the generic structure:

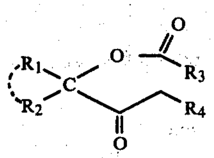

wherein $R_1$ and $R_2$ taken together complete a cycloalkyl moiety or methyl, dimethyl or trimethyl substituted cycloalkyl moiety containing five or six carbon atoms in the ring and wherein $R_3$ is $C_1$–$C_3$ lower alkyl and $R_4$ is methyl or hydrogen. Such compounds are provided by a novel process of our invention as shown by the reaction:

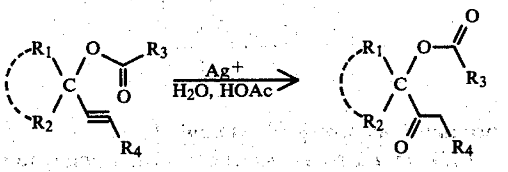

The compounds produced using the process of our invention are useful for their organoleptic properties in perfumes, perfumed articles, foodstuffs, foodstuff flavoring compositions, chewing gums, toothpastes, medicinal products, smoking tobaccos and smoking tobacco flavoring compositions, substitute smoking tobaccos and substitute smoking tobacco flavoring compositions.

In the perfumery art, there is a considerable need for substituents having sweet, fruity (figgy, raspberry-like), floral/rose-like, honey-like, rich, fruity (apple), green, floral/herbaceous, minty, camphoraceous, green, orris, leathery, earthy and peppery nuances with tobacco undertone. Specifically described herein are materials having such organoleptic profiles but which do not discolor with age. Such fragrance materials have a wide utilization in the presence of perfume compositions. A limited amount of such materials that give rise to these properties alone or in combination is available from natural sources, but the natural materials are subject to wide variations in quality, or are expensive and/or often in critically short supply.

In addition, there is a continuing search for food flavor compositions which can vary, fortify, modify, enhance, augment or otherwise improve the flavor and/or aroma of foodstuff, medicinal products, toothpastes, chewing gums and chewing tobaccos. To be satisfactory, such compositions should be stable, non-toxic and blendable with other ingredients to provide their own unique flavor and aroma nuances without detracting from the co-ingredients of the formulations in which they are used. Preferably, such compositions should be naturally occurring or present in natural foodstuffs so that their ingestible safety can be readily recognized. These materials should be capable of being synthesized in a simple and economical manner. The need for safe flavors in the raspberry, plum, strawberry and fruit juice-like flavor area is well known particularly in the ice cream and yogurt flavor areas. More specifically, there is a need for the development of non-toxic materials which can replace natural materials not readily available having floral, green, fruity, sweet, estery, strawberry-like and ionone-like aroma nuances with sweet, floral, green/berry, strawberry-like, plum-like, fruit juice-like, raspberry juice-like, green, bitter, fruity, estery, earthy, astringent and ionone-like flavor nuances.

In the tobacco flavoring art (pertaining to smoking tobaccos and substitute smoking tobaccos) there is a considerable need for adjuvants for smoking tobacco and substitute smoking tobacco having sweet, minty, cooling, spicey, anisic, berry-like, fruity, pineapple-like, woody, green, pepper-like and dill-like aromas and tastes prior to smoking and on smoking in both the main stream and in the side stream and resulting from adding the adjuvants to tobacco per se, to the wrapper or to the filter or to combinations of the parts of the smoking tobacco article.

The instant invention provides the foregoing which the prior art has heretofore failed to provide. Furthermore, nothing in the prior art shows the unexpected, unobvious and advantageous value for their organoleptic properties of the genus of compound defined according to the structure:

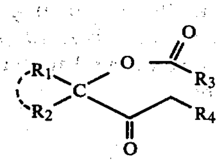

wherein $R_1$ and $R_2$ taken together complete a cycloalkyl moiety or a methyl, dimethyl or trimethyl cycloalkyl moiety containing five or six carbon atoms in the ring and wherein $R_3$ is $C_1$–$C_3$ lower alkyl and $R_4$ is methyl or hydrogen.

The prior art has already taught the reaction of alkyl substituted acetylene derivatives or mono-substituted acetylene derivatives to form ketones. Indeed, Stacy and Mikulec, Org. Synth. Coll., Vol. IV (1963) 13 teaches the reaction:

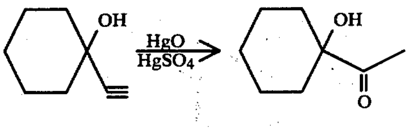

but does not discuss the use of metallic catalysts alternative to those containing mercury for such a reaction. Beilstein, Vol. 8, Supplement 3 teaches the reaction:

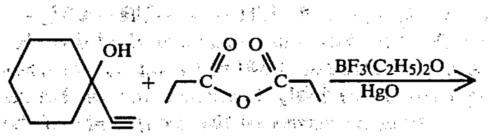

-continued

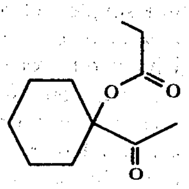

and Johnson "The Chemistry of Acetylenic Compounds", Vol. I, Edward Arnold & Company, London, 1946 at page 103 teaches the reaction:

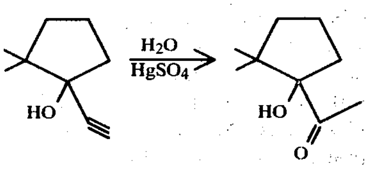

Nothing in the prior art shows the use in such a reaction of a silver ion catalyst without the addition of mineral acid. The silver is recoverable by precipitation of such salts as silver chloride or silver bromide. Such a mild acetylenic hydration is known in cases where catalysis using mercury compounds is used but use of silver is greatly advantageous particularly since mercury is toxic and there is a great likelihood of the mercury compound to contaminate equipment and create various hazardous situations.

Arctander "Perfume and Flavor Chemicals (Aroma Chemicals)", Vol. I, (1969), at monograph No. 37 discloses the use of acetyl cyclohexanol in perfumery and in perfumed articles indicating that acetyl cyclohexanol having the structure:

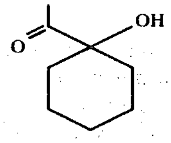

has a camphoraceous, minty, herbaceous, somewhat floral odor. Arctander further indicates that this material is produced by "hydration of 1-ethynyl-cyclohexanol".

United Kingdom Pat. No. 1,344,653 published on Jan. 23, 1974 discloses the use in perfumery of certain carbo cyclic odorants possessing the following structure:

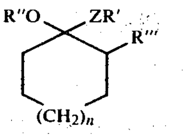
I where R' is hydrogen or methyl, R'' is hydrogen or $C_1$-$C_3$ alkanoyl, R''' is butyl, n is 0, 1 or 2, Z is one of the radicals —C≡C—, —CH=CH— or —$CH_2$—$CH_2$—.

Neither the Arctander disclosure nor the Givaudan United Kingdom Pat. No. 1,344,653 disclosure teaches either explicitly or implicitly the unexpected, unobvious and advantageous properties of the compounds of the instant application.

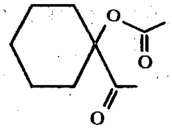

as well as the compound having the structure:

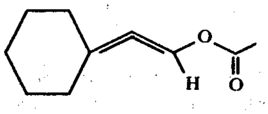

Figure 2:
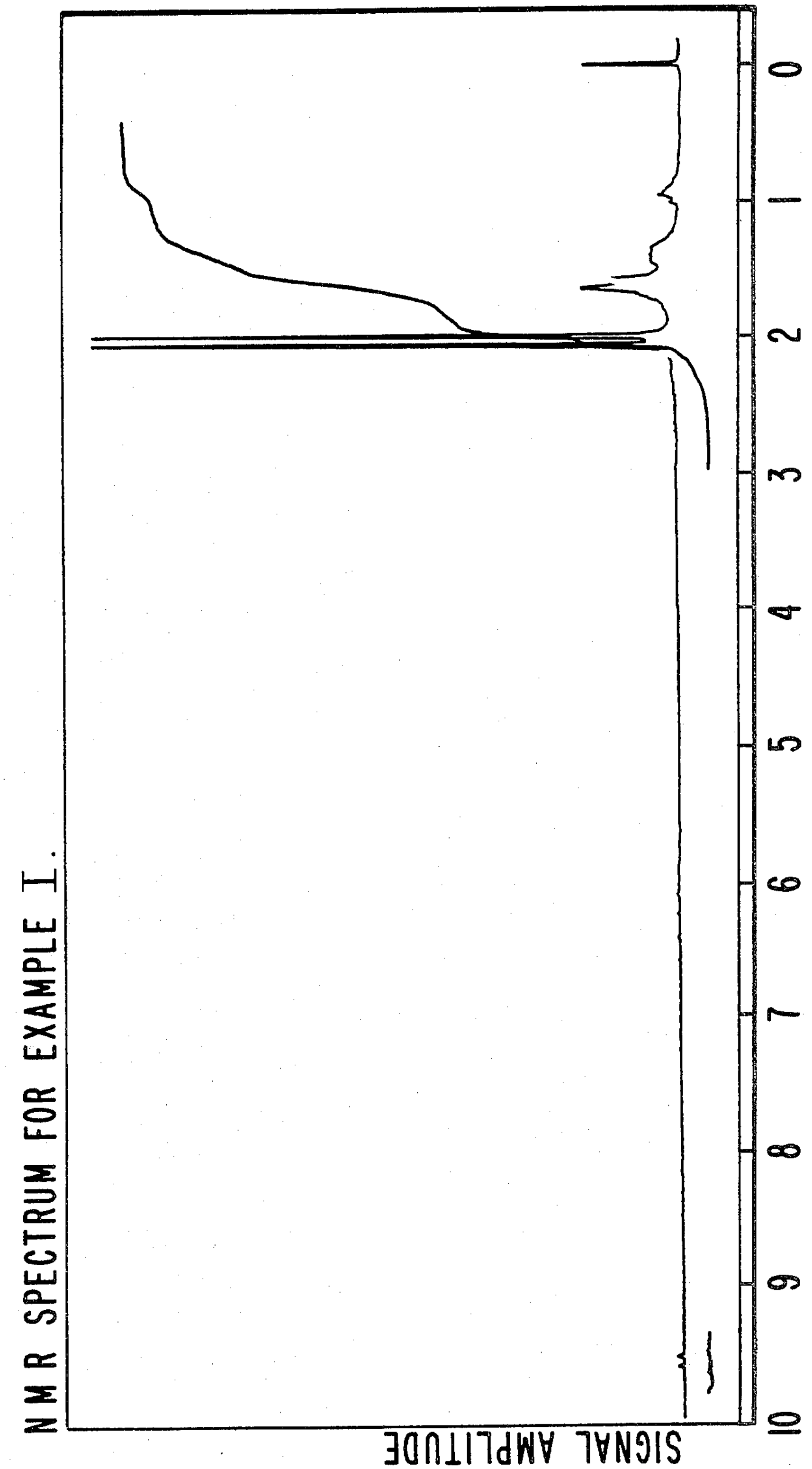

FIG. 2 is the NMR spectrum for the compound having the structure:

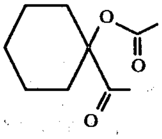

produced according to Example I.

Figure 3:
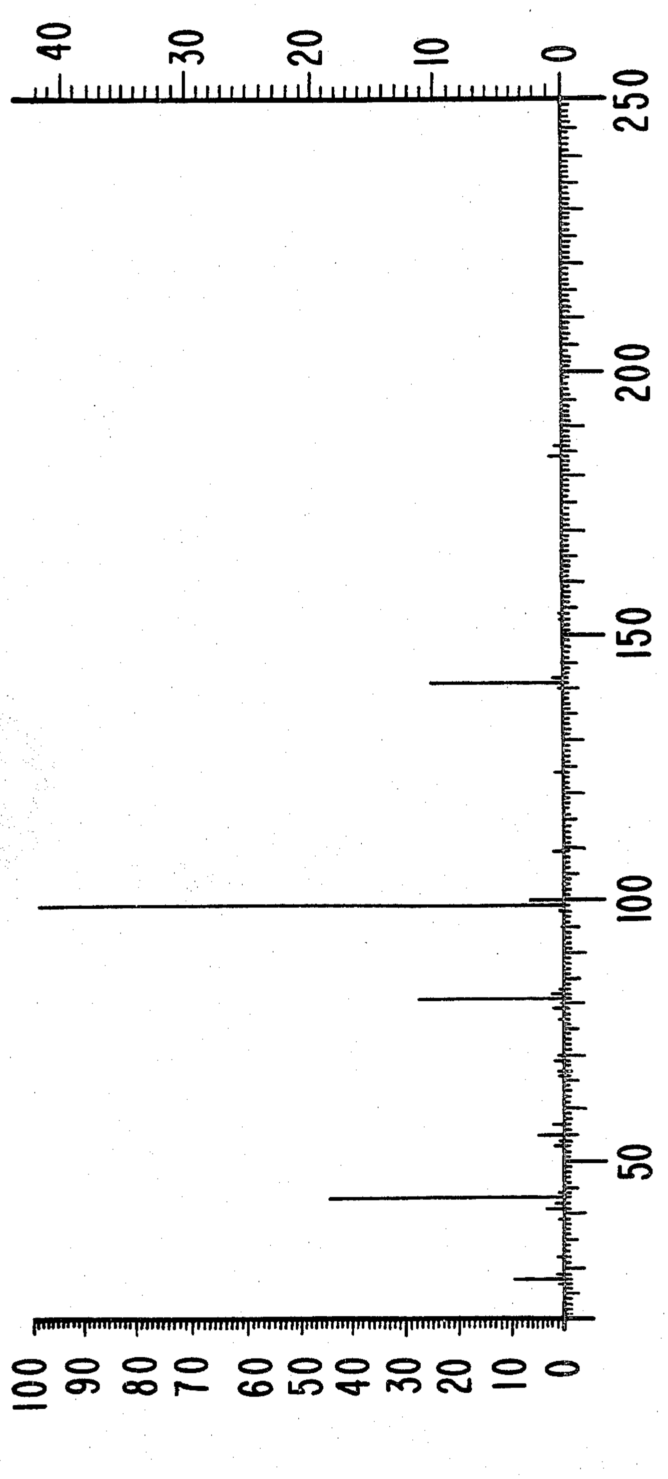

FIG. 3 is the mass spectrum for the compound having the structure:

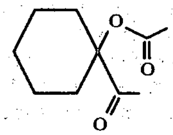

produced according to Example I.

Figure 4:
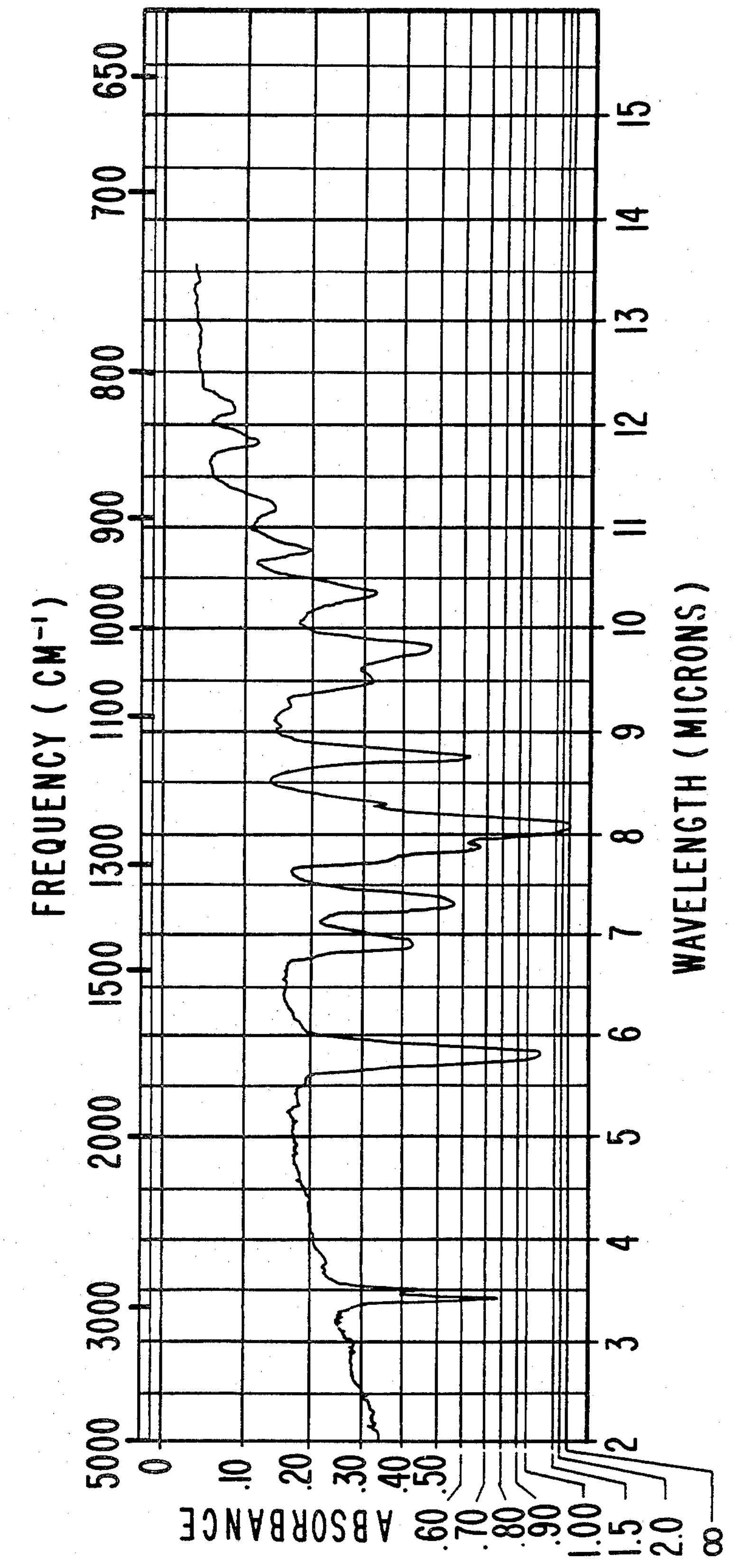

FIG. 4 is the infrared spectrum for the compound having the structure:

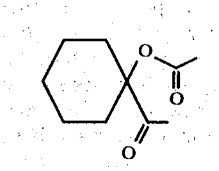

produced according to Example I.

Figure 5:
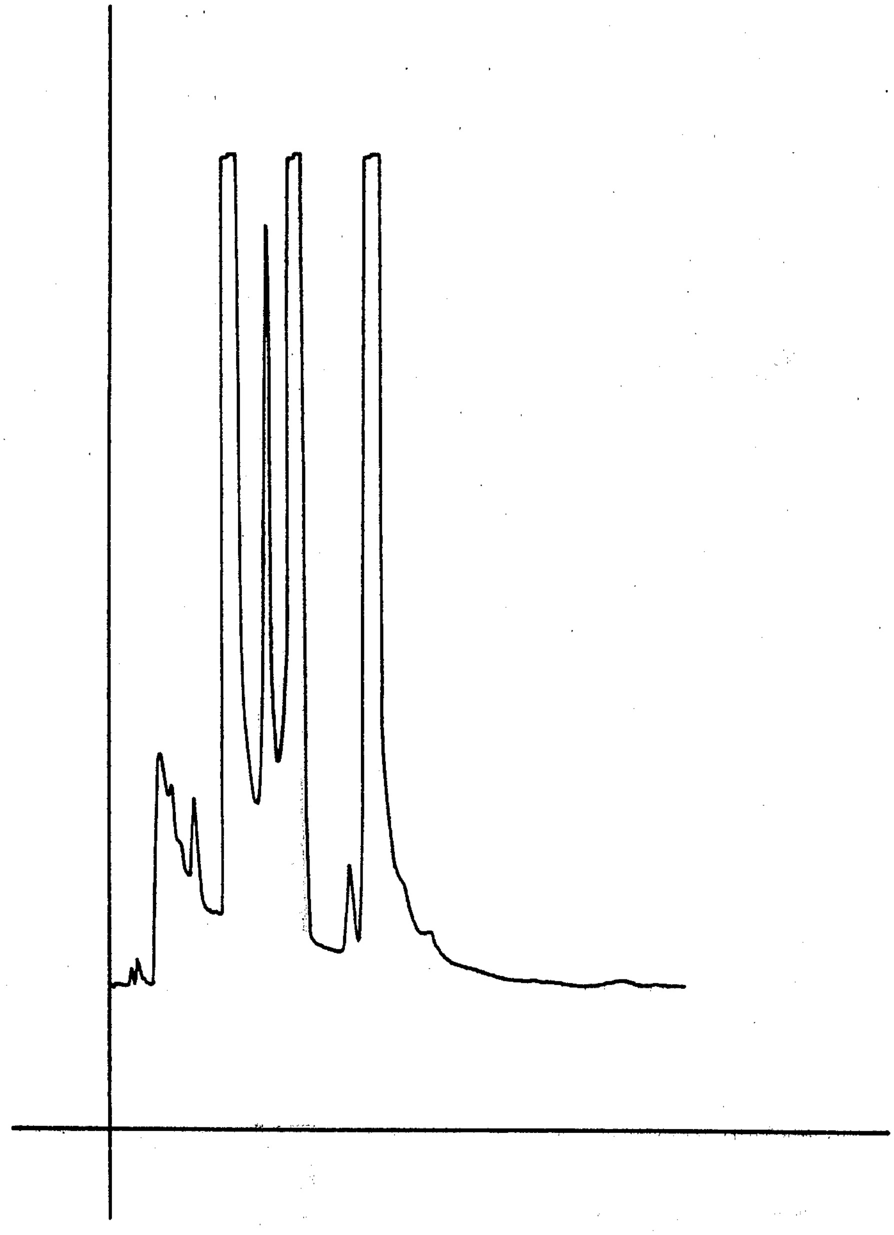

FIG. 5 is the GLC profile for the compound having the structure:

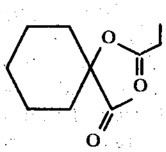

produced according to Example II.

Figure 6:
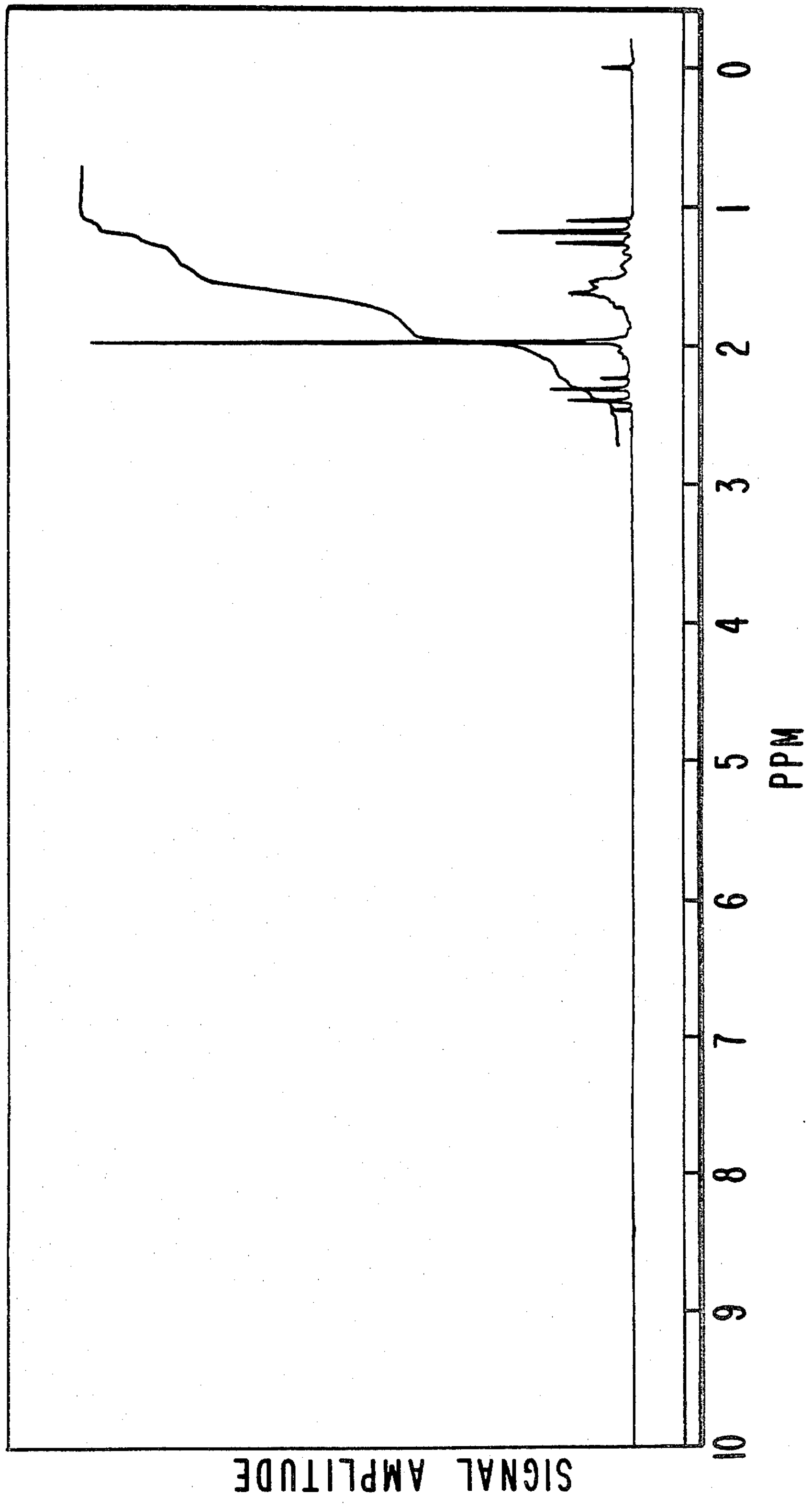

FIG. 6 is the NMR spectrum for the compound having the structure:

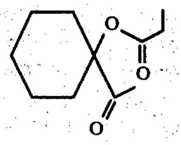

produced according to Example II.

Figure 7:
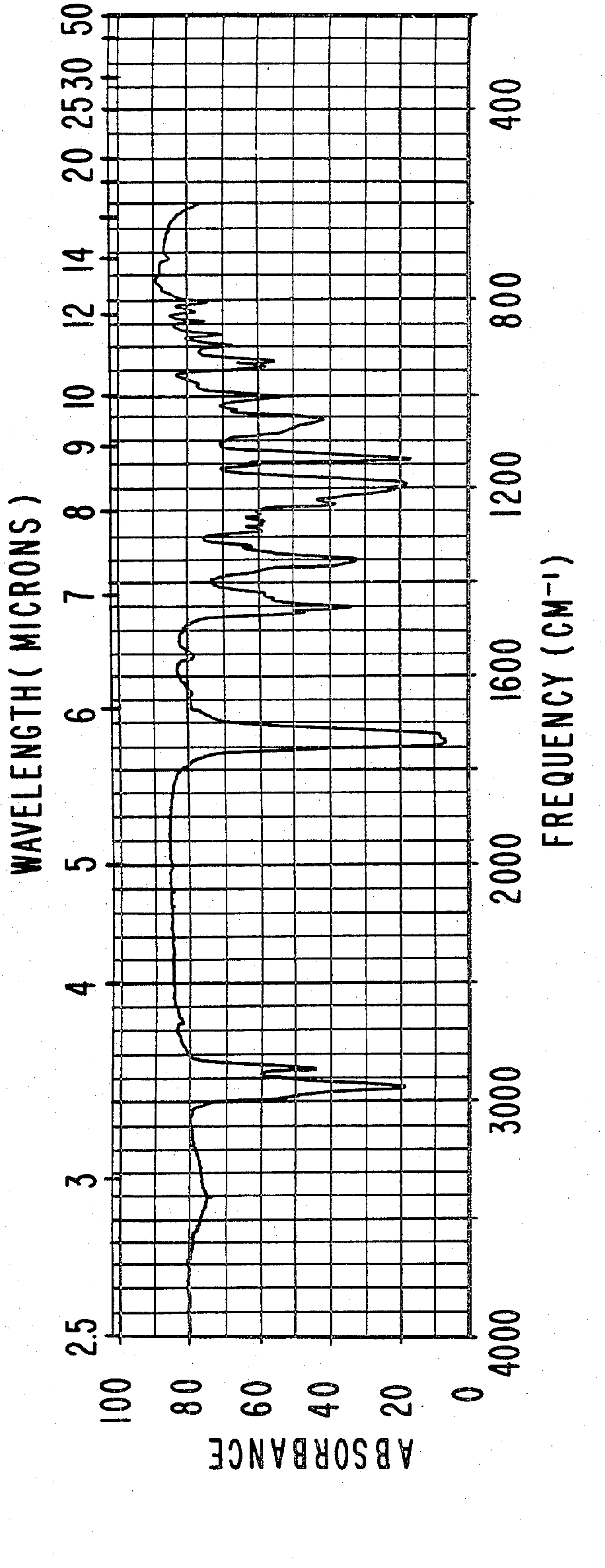

FIG. 7 is the infrared spectrum for the compound having the structure:

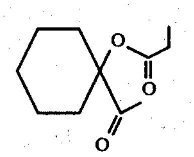

produced according to Example II.

Figure 8:
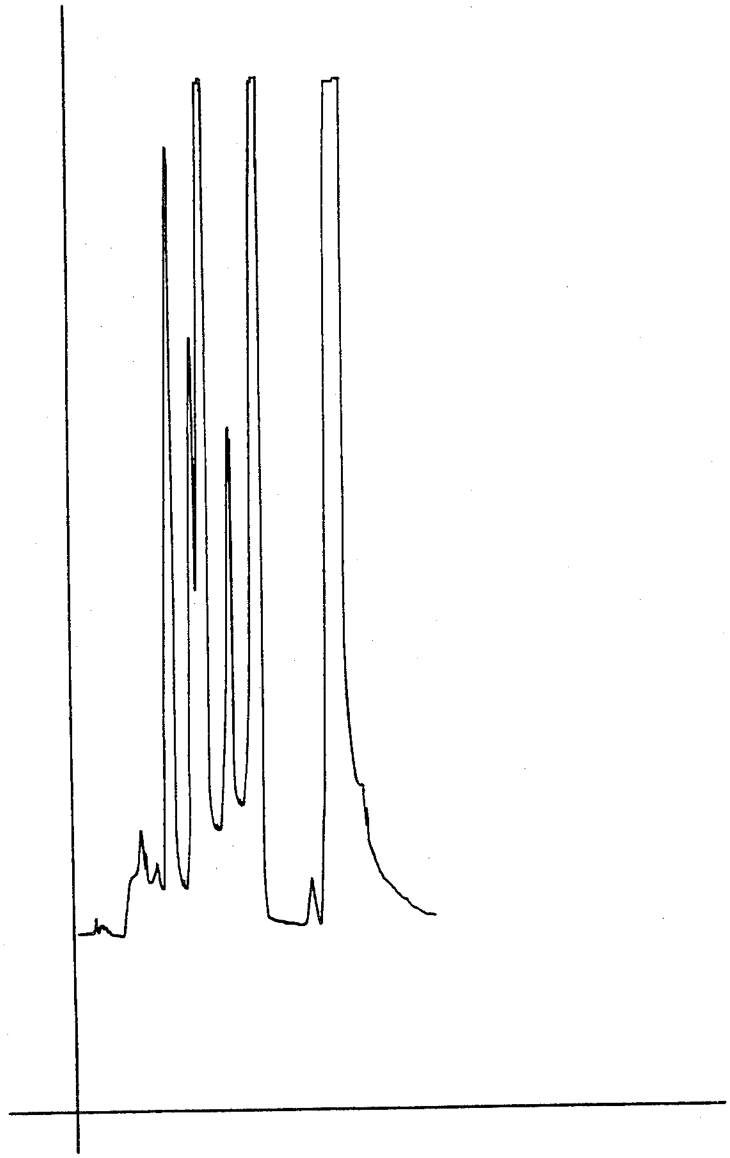

FIG. 8 is the GLC profile for the compound having the structure:

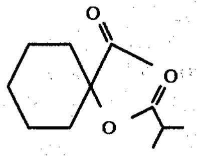

produced according to Example III.

Figure 9:
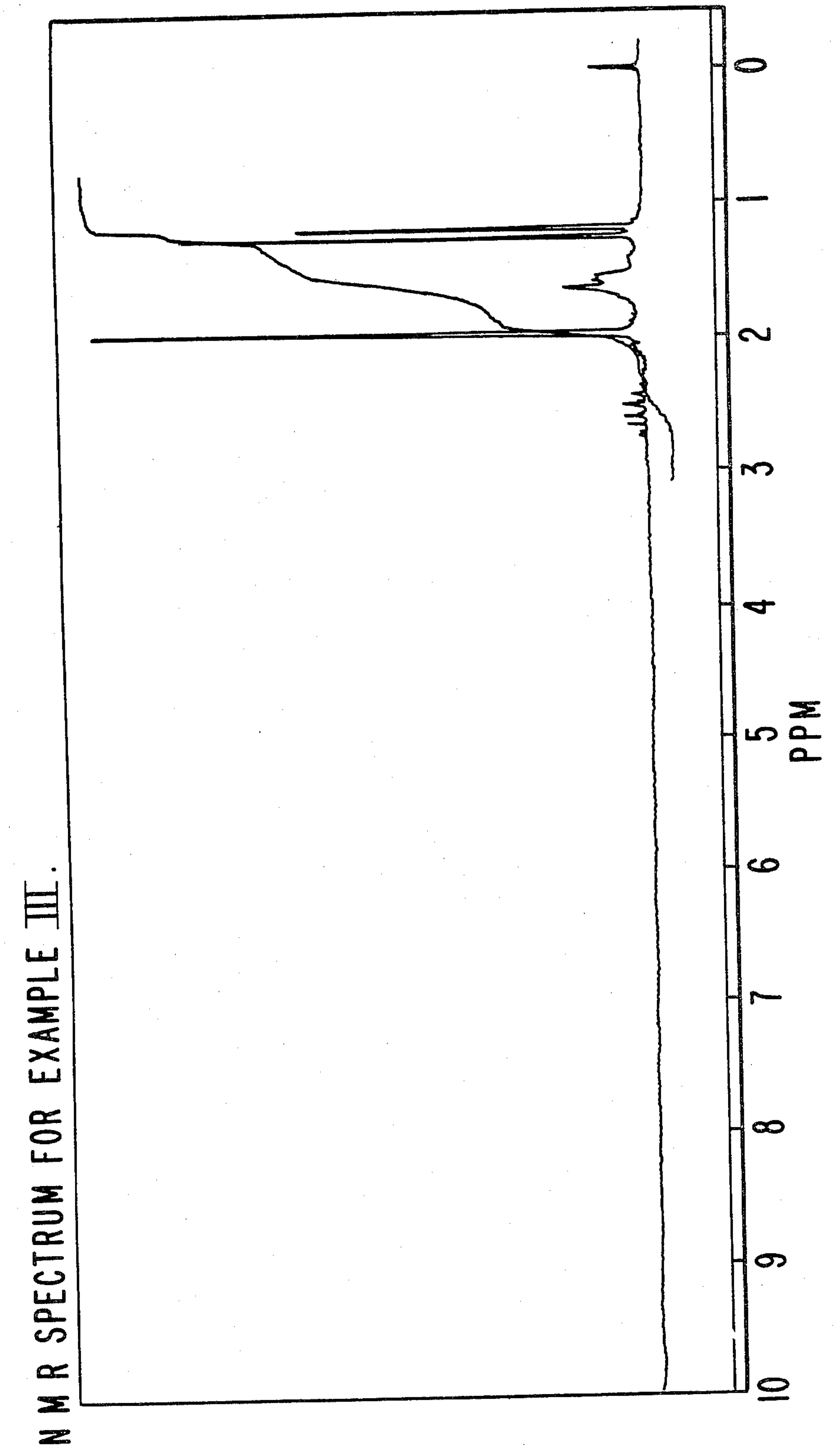

FIG. 9 is the NMR spectrum for the compound having the structure:

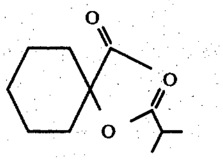

produced according to Example III.

Figure 10:
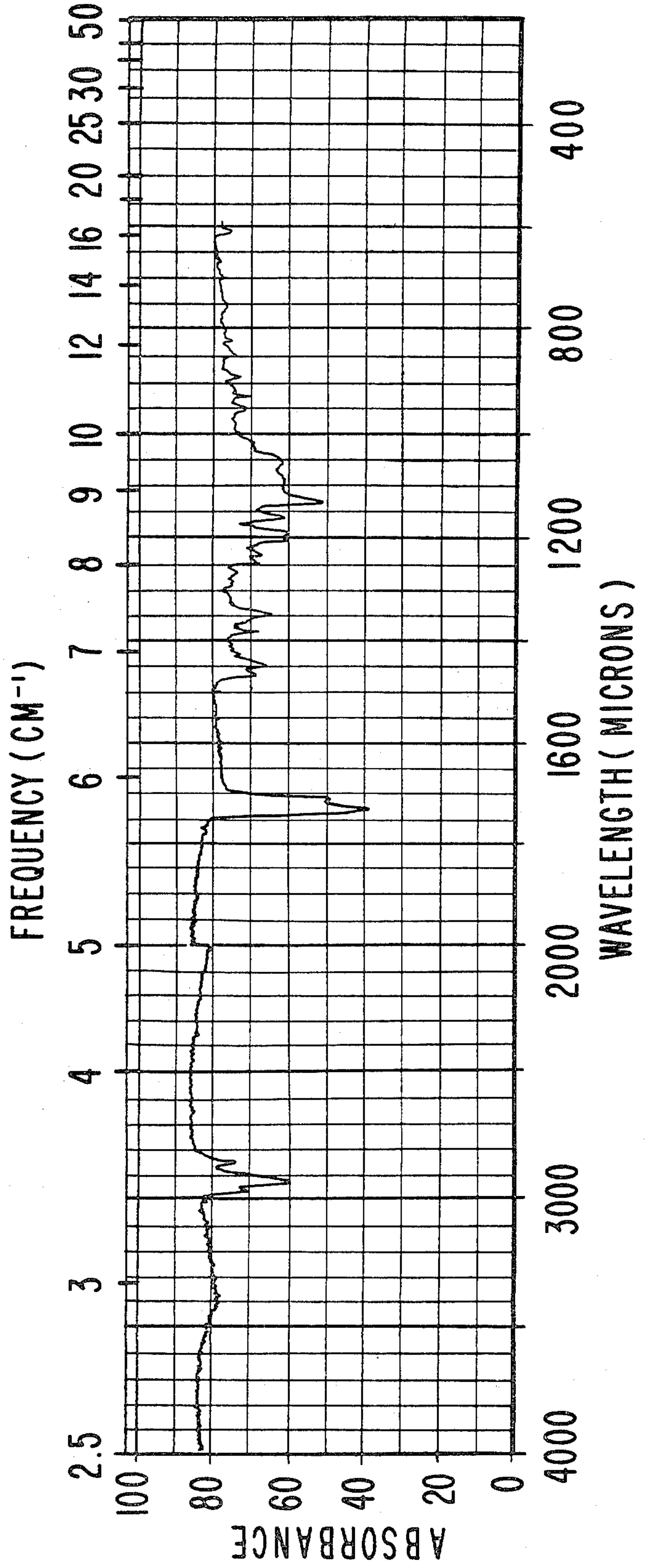

FIG. 10 is the infrared spectrum for the compound having the structure:

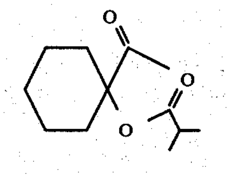

produced according to Example III.

Figure 11:
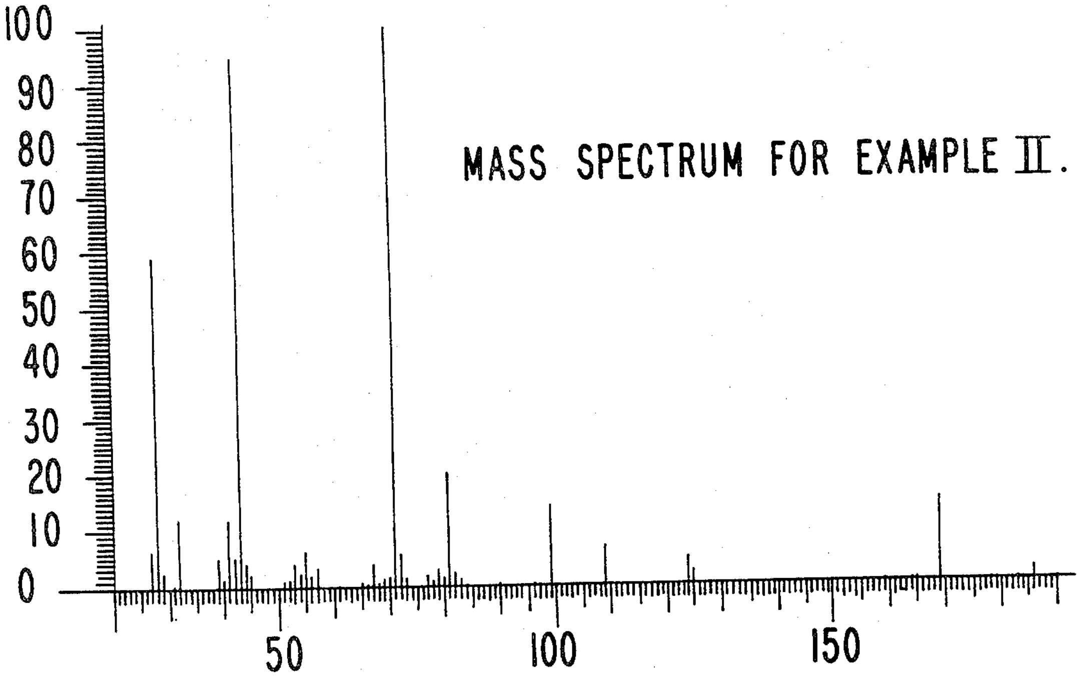

FIG. 11 is the mass spectrum for the compound having the structure:

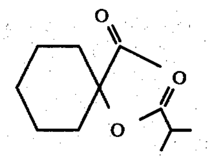

produced according to Example III.

Figure 12:
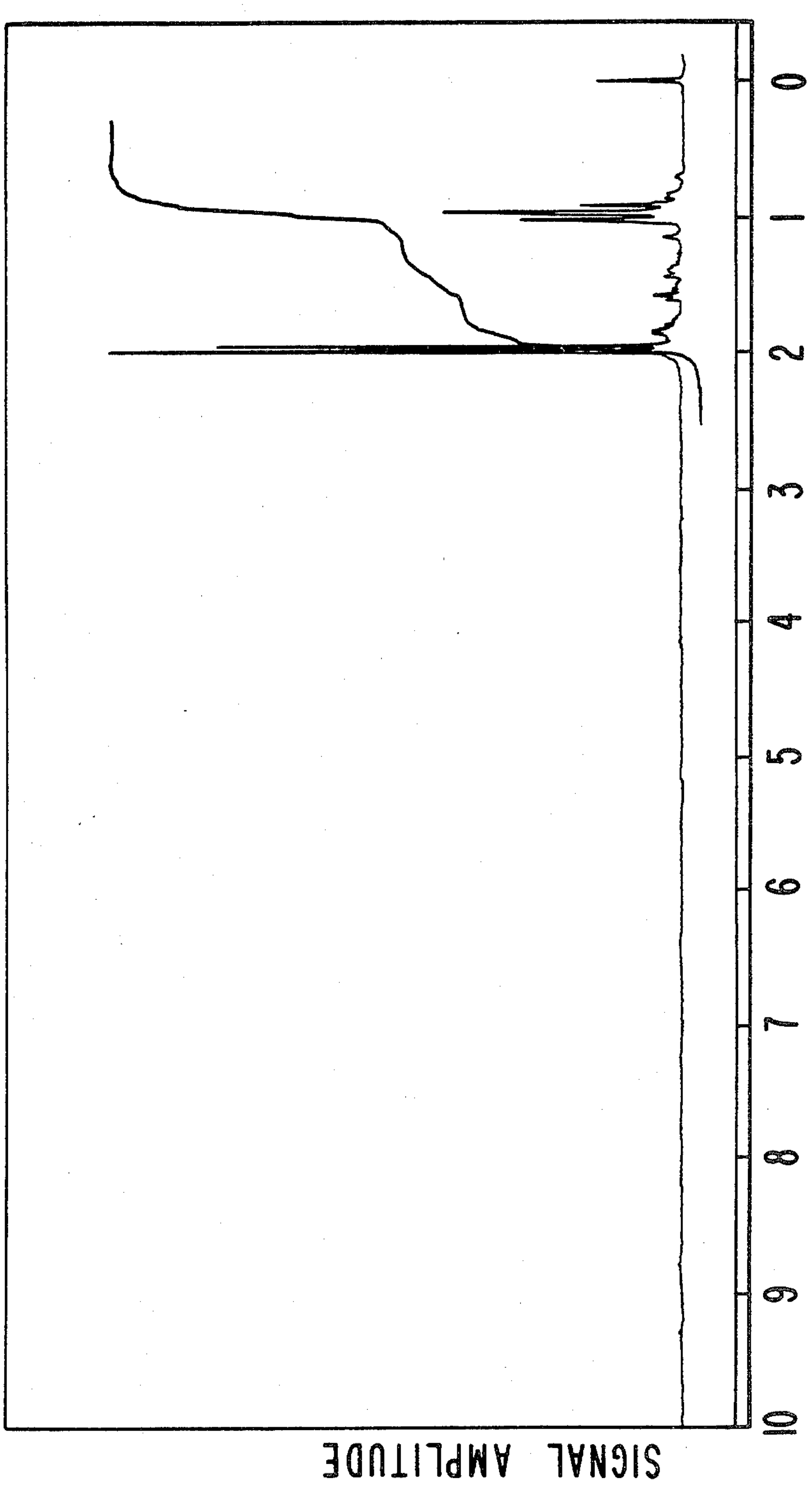

FIG. 12 is the NMR spectrum for the compound having the structure:

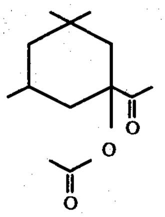

produced according to Example XXVIIID.

Figure 13:
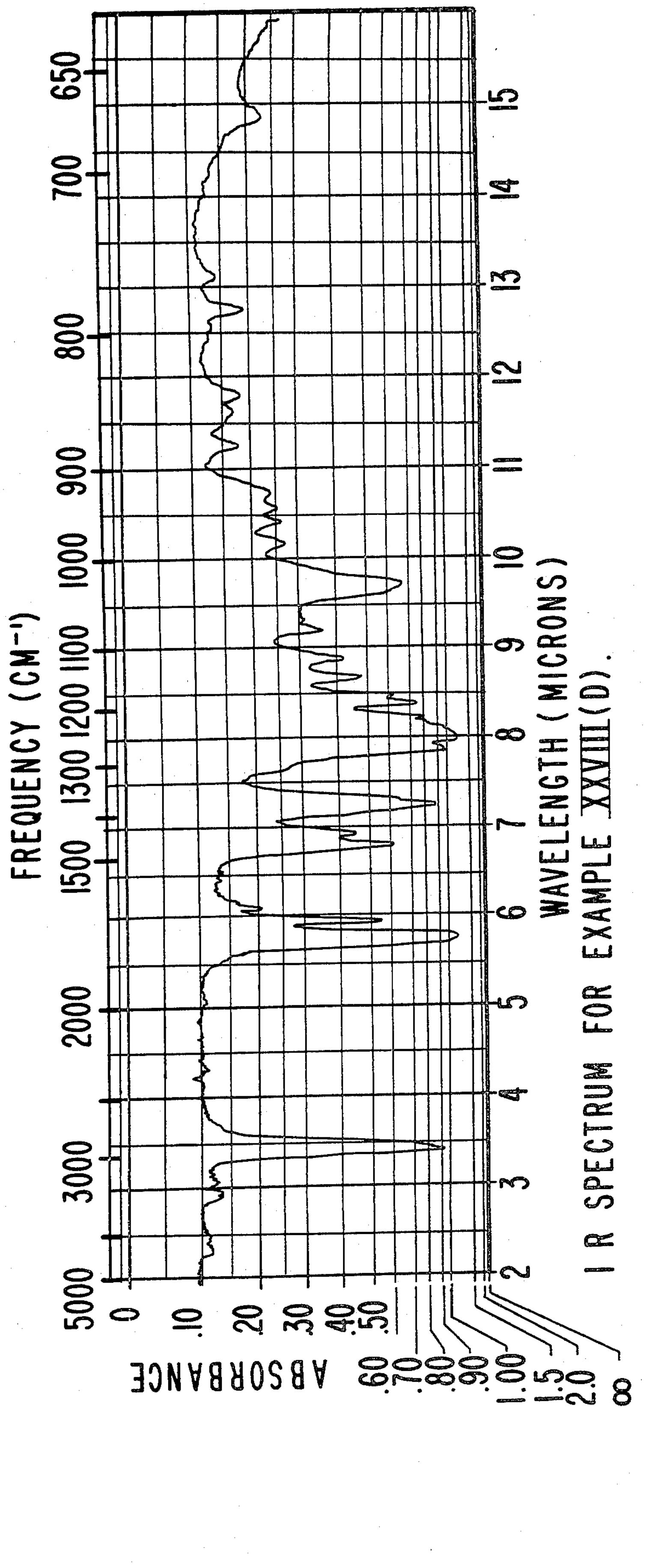

FIG. 13 is the infrared spectrum for the compound having the structure:

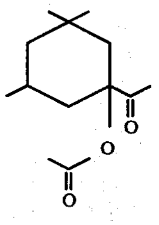

produced according to Example XXVIIID.

Figure 14:
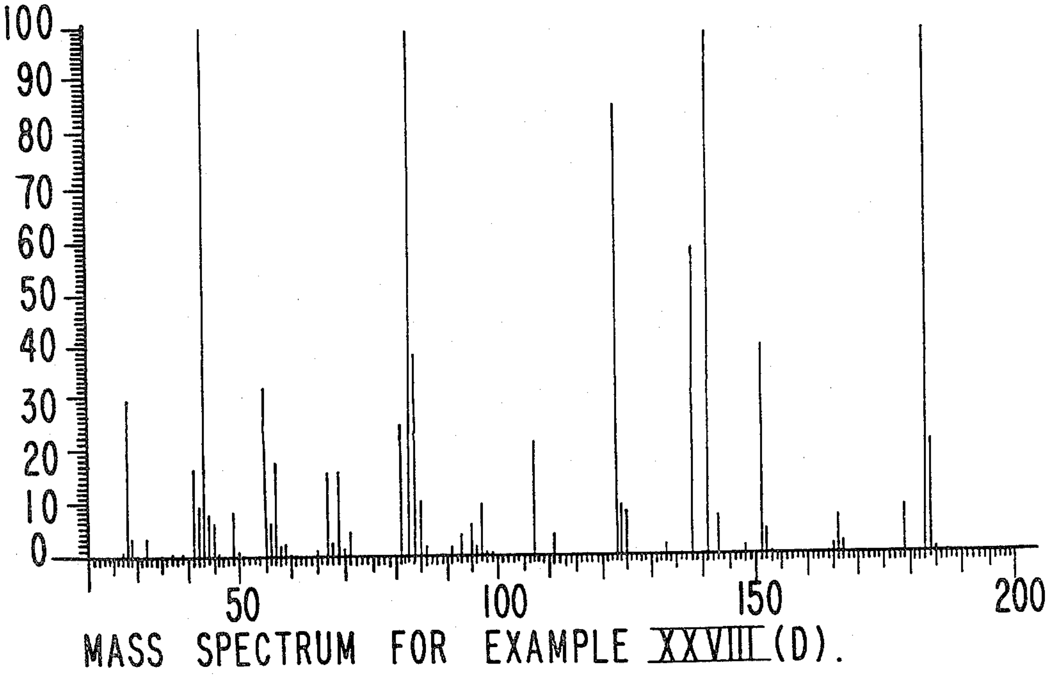

FIG. 14 is the mass spectrum for the compound having the structure:

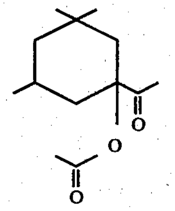

produced according to Example XXVIIID.

THE INVENTION

The present invention provides compounds having the generic structure:

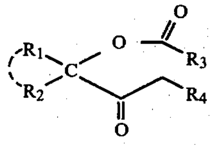

wherein $R_1$ and $R_2$ taken together complete a cycloalkyl moiety or a methyl, dimethyl or trimethyl cycloalkyl moiety containing five or six carbon atoms in the ring and wherein $R_3$ is $C_1$–$C_3$ lower alkyl and $R_4$ is methyl or hydrogen. The present invention also provides a process for preparing such compounds by hydrating the triple bond of the compounds defined according to the genus:

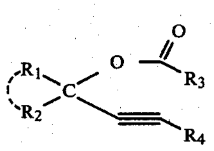

wherein $R_1$ and $R_2$ taken together complete a cycloalkyl moiety or a methyl, dimethyl or trimethyl cycloalkyl moiety containing five or six carbon atoms in the ring and wherein $R_3$ is $C_1$–$C_3$ lower alkyl and $R_4$ is methyl or hydrogen using aqueous silver ion catalyst in a weak organic acid media. Such a reaction is illustrated thusly:

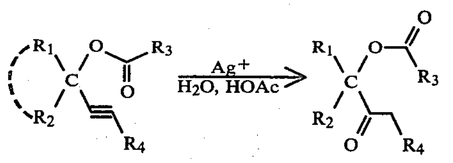

The 1-acylcycloalkyl alkanoates of our invention produced according to the process of our invention are capable of augmenting or enhancing the strawberry, raspberry or plum fruit flavors by imparting thereto a floral, green, fruity, sweet, estery, strawberry-like and/or ionone-like aroma characteristics and sweet, floral, green/berry, strawberry, plum-like, fruit juice-like, raspberry juice-like, green, bitter, fruity, estery, earthy, astringent and ionone-like flavor characteristics.

The 1-acylcycloalkyl alkanoates of our invention as well as mixtures thereof are also capable of modifying or enhancing the aroma characteristics of perfume compositions, colognes and perfumed articles (including soaps, anionic, cationic, nonionic and zwitterionic detergents, fabric softener compositions, optical brightener compositions and dryer-added fabric softener articles) by imparting thereto sweet, fruity (figgy, raspberry-like), floral/rose-like, honey-like, rich, fruity (apple), green, floral/herbaceous, minty, camphoraceous, green, orris, leathery, earthy and peppery aroma nuances with tobacco undertones thus fulfilling a need in the field of perfumery.

In smoking tobacco, smoking tobacco flavoring compositions, substitute smoking tobacco and substitute smoking tobacco flavoring compositions, the 1-acylcycloalkyl alkanoates of our invention produced according to the process of our invention impart sweet, minty, cooling, spicey, anisic, berry-like, fruity, pineapple-like, woody, green, pepper-like and dill-like aroma notes to smoking tobacco and substitute smoking tobaccos prior to smoking and on smoking in the main stream and in the side stream by causing the 1-acylcycloalkyl alkanoates to be in intimate contact with one or more parts of the smoking tobacco article, such as the wrapper, the tobacco section and/or the filter section.

The 1-acylcycloalkyl alkanoates of our invention are produced by reacting a compound having the structure:

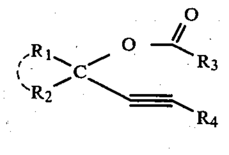

with a silver ion catalyst in aqueous media and in weak organic acid media. Thus, the concentration of silver ion (as silver nitrate, for example,) may vary from about 0.1% up to about 6 mole percent in the reactant solution. The temperature of reaction may vary from about 65° C. up to about 100° C. when using atmospheric pressure and may range up to about 120° C. when using pressures above atmospheric for carrying out this reaction. However, pressures above atmospheric do not create any particular advantages in the carrying out of this reaction. The reaction is carried out in a weak organic acid such as acetic acid, propionic acid, n-butyric acid or isobutyric acid. The ratio of water:organic acid is such that a homogeneous mixture must be obtained at the reaction temperature used when the starting material is added. The ratio of water to organic acid (mole ratio) may vary from about 0.1:1 up to about 2:1 water:organic acid.

The time of reaction may vary from about 2 hours up to about 6 hours depending on the desired yield of end product. During the first hour, the acetylenic derivative having the generic structure:

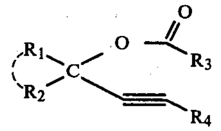

is added to the aqueous solution containing the silver ion and the organic acid. Initially, the mixture of silver ion and organic acid is heated up to the desired temperature at which the reaction is to be carried out. While the reaction mass temperature is maintained, the acetylenic compound having the generic structure is slowly added thereto over a period of between one and three hours. After the addition of acetylenic compound having the structure:

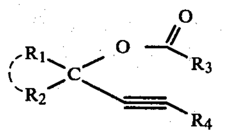

the reaction mass preferably is continued to be stirred at the temperature of the reaction until analysis (e.g., via GLC) indicates that no additional acyl cycloalklyl alkanoate having the generic structure:

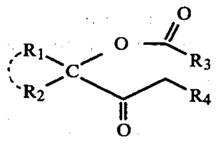

is formed. During the reaction, in addition to the 1-acylcycloalkyl alkanoate having the structure:

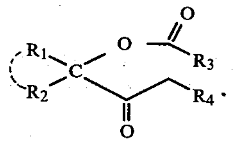

being formed, allenic compounds may also be formed and these allenic compounds have the structure, for example:

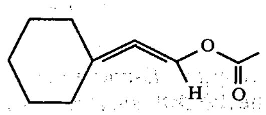

The allenic compounds, when they are formed, are removed from the reaction mass after appropriate work-up of the reaction mass by means of fractional distillation. In addition, the acyl cycloalkyl alkanoates having the generic structure:

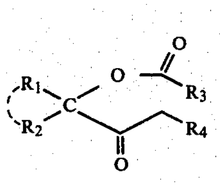

is purified by routine fractional distillation.

The compounds of our invention may also be formed by esterification with the appropriate alkanoic acid anhydride or alkanoyl halide of the hydroxy acetyl cyclohexane or hydroxy acetyl cyclopentane, for example, the compound having the structure:

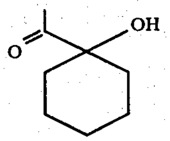

When one or more of the 1-acylcycloalkyl alkanoates of our invention is used as a food flavor adjuvant, the nature of the co-ingredients included with said one or more 1-acylcycloalkyl alkanoates in formulating the product composition will also serve to alter the organoleptic characteristics of the ultimate foodstuffs treated therewith. As used herein, in regard to flavors, the term "alter" in its various forms means "supplying or imparting flavor character or notes to otherwise bland relatively tasteless substance or augmenting the existing flavor characteristic where a natural flavor is deficient in some regard or supplementing the existing flavor impression to modify its quality, character or taste".

As used herein, the term "foodstuff" includes both solid and liquid ingestible materials which usually do but need not have nutritional value. Thus, foodstuffs include soups, convenience foods, beverages, dairy products, candies, fruits, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propy gallate and the like, and sequestrants, e.g., citric acid.

Thickener compounds include carriers, binders, protective colloids, suspending agents, emulsifiers and the like, e.g., agaragar; carrageenan; cellulose and cellulose derivatives such as carboxymethyl cellulose and methyl cellulose; natural and synthetic gums such as gum arabic, gum tragacanth; gelatine; proteinaceous materials; lipids; carbohydrates; starches pectins, and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, $\beta,\beta$-dimethylacrolein, hexanal, 2-hexenal, cis-3-hexenal, 4(p-hydroxyphenyl)-2-butanone, $\alpha$-ionone, $\beta$-ionone, and 2-pentenal; alcohols, such as 1-butanol, trans-2-buten-1-ol, ethanol, gernaiol, 1-hexanol, cis-3-hexen-1-ol, 3-methyl-3-buten-1-ol, 1-pentanol, 1-penten-3-ol; esters, such as butyl acetate, ethyl acetate, ethyl butyrate, ethyl crotonate, ethyl propionate, 2-hexenyl acetate, 2-hexenyl butyrate, hexyl acetate; hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate, and terpenyl acetate; essential oils such as jasmine absolute, rose absolute, orris absolute, lemon essential oil and vanilla; lactones; sulfides, e.g., methyl sulfide and other materials such as maltol and citral as well as natural raspberry oil and natural strawberry juice concentrate.

The specific flavoring adjuvants selected for use may be either solid or liquid, depending upon the desired physical form of the ultimate product, i.e., foodstuff, whether simulated or natural, and should, in any event, be capable of providing an environment in which the one or more 1-acylcycloalkyl alkanoates of our invention can be disbursed or admixed to provide a homogeneous medium. In addition, selection of one or more adjuvants, as well as the quantities thereof, will depend upon the precise organoleptic raspberry character, strawberry character or plum character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of one or more 1-acylcycloalkyl alkanoates of our invention employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirement is that amount which is effective, i.e., sufficient to alter the organoleptic characteristics of the parent composition, whether foodstuff per se or flavoring composition. Thus, the use of insufficient quantities of one or more 1-acylcycloalkyl alkanoates will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus and with respect to ultimate food compositions, it has been found that quantities of one or more 1-acylcycloalkyl alkanoates ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein the one or more 1-acylcycloalkyl alkanoates is added to the foodstuff as an integral component of the flavoring composition, it is, of course, essential that the total quantity of flavoring composition employed be sufficient to yield an effective one or more 1-acylcycloalkyl alkanoate concentration in the foodstuff product.

Food flavoring compositions prepared in accordance with the present invention preferably contain one or more 1-acylcycloalkyl alkanoate in concentrations ranging from about 0.05% up to about 10% by weight based on a total weight of said flavoring composition.

The compositions described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing one or more 1-cyclocycloalkyl alkanoate with, for example, gum arabic, gum tragacanth, carrageenan and the like and thereafter spray-drying the resultant mixture whereby to obtain the particulate solid product. Prepared flavor mixes in powder form, e.g., a raspberry flavored powder are obtained by mixing dried solid, components, e.g., starch, sugar and the like and one or more 1-acylcycloalkyl alkanoate in a dry blender until the requisite degree of uniformity is achieved.

It is presently preferred to combine the one or more 1-acylcycloalkyl alkanoate with the following adjuvants:

Parahydroxybenzyl acetone;
Vanillin;
Maltol;
α-Ionone;
β-Ionone;
Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-dimethyl-2-methylene-3-cyclohexen-1-yl)-2-butanone
2-(4-hydroxy-4-methylpentyl)norbornadiene produced according to Example I of U.S. Pat. No. 3,911,028
β-Damascone (1-crotonyl-2,6,6-trimethylcyclohex-1-ene);
β-Damascenone (1-crotonyl-2,6,6-trimethylcyclohexa-1,3-diene);
Beta-cyclohomocitral (2,6,6-trimethylcyclohex-1-ene carboxaldehyde)
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene);
Cis-2-3-methyl pentenoic acid;
Ethyl-2-methyl-3-pentenoate; and
Isobutyl-cis-2-methyl-3-pentenoate One or more 1-acylcycloalkyl alkanoate derivatives prepared in accordance with the process of our invention and one or more auxiliary perfume ingredients including, for example, alcohols other than the 1-acylcycloalkyl alkanoate derivatives of our invention; aldehydes, ketones, terpenic hydrocarbons, nitriles, esters other than the 1-acylcycloalkyl alkanoate derivatives of our invention, lactones, natural essential oils and synthetic essential oils may be admixed so that the combined odors of the individual components produce a pleasant and desired fragrance, particularly, and preferably, in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, one or more 1-acylcycloalkyl alkanoate derivatives prepared in accordance with the process of our invention, can be used to alter, modify or enhance the aroma characteristics of a perfume composition, for example, by utilizing or moderating the olfactory reaction contributed by another ingredient in the composition.

The amount of one or more 1-acylcycloalkyl alkanote derivatives prepared in accordance with the process of our invention which will be effective in perfume compositions as well as in perfumed articles (e.g., anionic, nonionic, cationic and zwitterionic solid or liquid detergents, soaps, fabric softener compositions, dryer-added fabric softener articles, optical brightener compositions and textile sizing agents) and colognes depends on many factors, including the other ingredients, their amounts and the effects which are desired. It has been found that perfume compositions containing as little as 0.01% of one or more 1-acylcycloalkyl alkanoate derivatives prepared in accordance with the process of our invention and less than 50% of one or more 1-acylcycloalkyl alkanoate derivatives prepared in accordance with the process of our invention or even less (e.g., 0.005%) can be used to impart a sweet, fruity (figgy, raspberry), floral/rose-like, honey-like, rich, fruity (apple-like), green, floral/herbaceous, minty, camphoraceous, green, orris, leathery, earthy and peppery nuances with tobacco undertones to soaps, cosmetics, solid or liquid anionic, cationic, nonionic or zwitterionic detergents, fabric softener compositions, fabric softener articles, optical brightener compositions, textile sizing compositions or other products. The amount employed can range up to 70% of the fragrance components and will depend on considerations of cost, nature of the end product, the effect desired on the finished product and the particular fragrance sought.

One or more 1-acylcycloalkyl alkanoate derivatives prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 0.2% of one or more 1-acylcycloalkyl alkanoate derivatives prepared in accordance with the process of our invention will suffice to impart an intense floral, fruity, minty/camphoraceous and green aroma to rose formulations. Generally, no more than 6% of one or more 1-acylcycloalkyl alkanoate derivatives of our composition based on the ultimate end product is required in the perfumed article composition.

In addition, the perfume composition or fragrance composition of our invention can contain a vehicle or carrier for one or more 1-acylcycloalkyl alkanoate derivatives prepared in accordance with the process of our invention. The vehicle can be a liquid, such as a non-toxic alcohol, a non-toxic glycol, or the like. The carrier can also be an absorbent solid, such as a gum (e.g.) gum arabic) or components for encapsulating the composition (such as gelatin) as by coacervation.

It will thus be apparent that one or more 1-acylcycloalkyl alkanoate derivatives prepared in accordance with the process of our invention can be utilized to alter, modify or enhance sensory properties, particularly organoleptic properties, such as flavor(s) and/or fragrance(s) of a wide variety of consumable materials.

Furthermore, one or more 1-acylcycloalkyl alkanoate derivatives prepared in accordance with the process of our invention are capable of supplying and/or potentiating certain flavor and aroma notes usually lacking many smoking tobacco flavors and substitute tobacco flavors heretofore provided.

As used herein in regard to smoking tobacco flavors, the terms "alter" and "modify" in their various forms means "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired sweet, minty, cooling, spicey, anisic, berry-like, fruity, pineapple-like, woody, green, peper or dill-like aroma and taste nuances prior to and on smoking in both the main stream and the side stream are created or enhanced and may be readily controlled and maintained at the desired uniform level regardless of variations in the tobacco components of the blend.

This invention further provides improved smoking tobacco additives and methods whereby various sweet, minty, cooling, spicey, anisic, berry-like, fruity, pineapple-like, woody, green, pepper and dill-like notes are imparted (on smoking in the main stream and the side stream) to smoking tobacco products and may be readily varied and controlled to produce the desired uniform flavor characteristics, particularly insofar as "oriental" like tobacco characteristics are concerned.

In carrying out this aspect of our invention, we add to smoking tobacco materials or a suitable substitute therefor (e.g., dried lettuce leaves) an aroma and flavor additive containing as an active ingredient at least one or more 1-acylcycloalkyl alkanoate derivative prepared according to the process of our invention.

In addition to the one or more 1-acylcycloalkyl alkanoate derivatives prepared in accordance to the process of our invention, other flavoring and aroma additives may be added to the smoking tobacco materials or substitute therefor either separately or in admixture with the one or more 1-acylcycloalkyl alkanoate derivatives prepared in accordance to the process of our invention as follows:

(i) Synthetic Materials

Beta-ethyl-cinnamaldehyde;
Beta-cyclohomocitral;
Eugenol;
Dipentene;
β-Damascenone;
β-Damascone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;

Dodecahydro-3a,6,6,9a-tetramethylnaphtho[2,1,b]-furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils

Celery seed oil;
Coffee extract;
Bergamot oil;
Cocoa extract;
Nutmeg oil; and
Origanum oil An aroma and flavoring concentrate containing one or more 1-acylcycloalkyl alkanoate derivatives prepared in accordance with the process of our invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of one or more 1-acylcycloalkyl alkanoate derivatives produced to smoking tobacco material is between 250 ppm and 1,500 ppm (0.025%–0.15%) of the active ingredients to the smoking tobacco material. We have further found that satisfactory results are obtained if the proportion by weight of the sum total of one or more 1-acylcycloalkyl alkanoate derivatives prepared in accordance with the process of our invention is between 2,500 and 15,000 ppm (0.025%–1.50%).

Any convenient method for incorporating one or more 1-acylcycloalkyl alkanoate derivatives prepared in accordance with the process of our invention in the tobacco product may be employed. Thus, one or more 1-acylcycloalkyl alkanoate derivatives of our invention taken alone or along with other flavoring additives may be dissolved in a suitable solvent, such as ethanol, pentane, diethyl ether and/or other volatile organic solvents and the resulting solution may either be sprayed on the cured, cased and blended tobacco material or the tobacco material may be dipped into such solution. Under certain circumstances, a solution containing one or more 1-acylcycloalkyl alkanoate derivatives prepared in accordance with the process of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have one or more 1-acylcycloalkyl alkanoate derivatives prepared in accordance with the process of our invention in excess of the amounts or concentrations above-indicated so that when blended with other tobaccos, the final product will have the percentage within the indicated range.

In accordance with one specific example of our invention, an aged, cured and shredded domestic Burley tobacco is sprayed with a 20% ethyl alcohol solution of a 25:25:50 (mole:mole:mole) mixture of 1-acetylcyclohexyl acetate:1-acetylcyclohexyl propionate:1-acetylcyclohexyl isobutyrate, respectively, in an amount to provide a tobacco composition containing 800 ppm by weight of said 1-acetylcyclohexyl alkanoate on a dry basis.

Thereafter, the alcohol is removed by evaporation and the tobacco is manufactured into cigarettes by the usual techniques. The cigarette when treated as indicated has a desired and pleasing aroma prior to smoking which can be described as sweet, minty, cooling, spicey, anisic, berry-like, fruity, pineapple-like, woody, green, pepper-like and dill and on smoking in the main stream and in the side stream a sweet, spicey, oriental-like, Turkish tobacco-like aroma.

While our invention is particularly useful in manufacture of smoking tobacco, such as cigarette tobacco, cigar tobacco and pipe tobacco, other smoking tobacco products formed from sheeted tobacco dust or fines may also be used. Likewise, one or more 1-acylcycloalkyl alkanoate derivatives prepared in accordance with the process of our invention can be incorporated with materials such as filter tip materials, seam paste, packaging materials and the like which are used along with tobacco to form a product adapted for smoking. Furthermore, one or more 1-acylcycloalkyl alkanoate derivatives prepared in accordance with the process of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following examples serve to illustrate our invention but our invention is only intended to be limited as indicated in the appended claims. All parts and percentages given herein are by weight unless otherwise specified.

EXAMPLE I

Preparation of 1-Acetyl-cyclohexyl Acetate

Reaction:

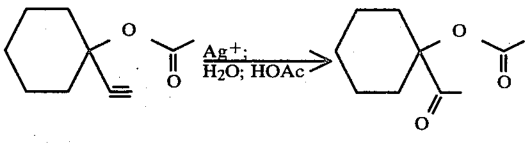

Into a 500 ml reaction flask equipped with thermometer, stirrer and addition funnel and heating mantle is placed 75 ml water, 75 ml acetic acid and 1.5 grams of silver nitrate. The resulting mixture is heated to 80° C. While maintaining the temperature of the reaction mass at 80° C., 150 grams of 1-ethynyl cyclohexyl acetate is added over a period of 1.5 hours. The reaction mass is then quenched with 230 ml of a 20% aqueous sodium chloride solution causing the silver ion catalyst to precipitate as, interalia, silver chloride. The reaction mass is then filtered through a Buchner funnel. The resulting liquid exists in two phases, an organic phase and an aqueous phase. The organic phase is washed with two 250 ml volumes of water followed by one 250 ml saturated sodium bicarbonate solution portion followed by one 250 ml saturated sodium chloride solution.

Figure 1:
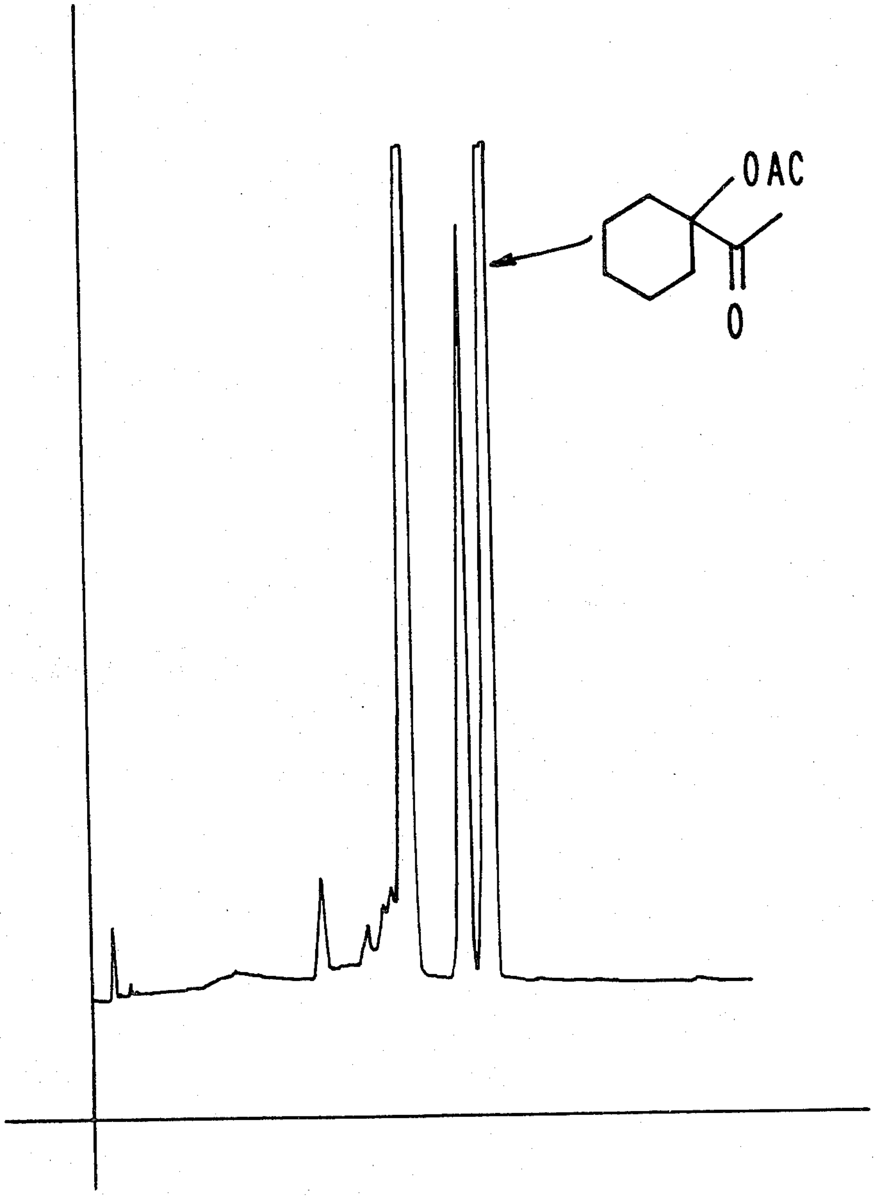
FIG. 1 is the GLC profile for the reaction product produced according to Example I containing the compound.

FIG. 1 sets forth the GLC profile for the resulting product. (Conditions: 100°-200° C. at 8° C. per minute/10% Carbowax column).

The resulting material is then distilled on a 3 foot distillation column yielding the following fractions:

| Fraction No. | Vapor Temp. | Liquid Temp. | mm Hg Pressure | Reflux Ratio | Wgt. of Fraction |
|---|---|---|---|---|---|
| 1 | 30/57 | 56/96 | 3.0 | 10:1 | 8.9 |
| 2 | 56 | 93 | 3.0 | 10:1 | 9.9 |
| 3 | 68 | 100 | 3.0 | 10:1 | 3.8 |
| 4 | 76 | 100 | 3.0 | 10:1 | 11.0 |
| 5 | 78 | 98 | 3.0 | 10:1 | 10.2 |
| 6 | 79 | 99 | 3.1 | 10:1 | 14.7 |
| 7 | 80 | 99 | 3.1 | 10:1 | 14.2 |
| 8 | 78 | 98 | 3.0 | 10:1 | 10.8 |
| 9 | 77 | 98 | 3.0 | 10:1 | 14.0 |
| 10 | 79 | 100 | 3.1 | 10:1 | 12.3 |
| 11 | 40 | 220 | 3.0 | 10:1 | 8.0 |

Of the foregoing eleven fractions, "A" represents forerun, "B" represents the compound having the structure:

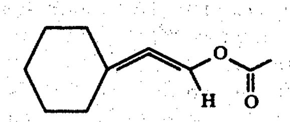

and "C" represents the compound having the structure:

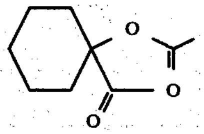

thusly:

| Fraction No. | Weight of Fraction | "A" % | "B" % | "C" % |
|---|---|---|---|---|
| 1 | 8.9 | 95.6 | 1.1 | 3.3 |
| 2 | 9.9 | 100.0 | — | — |
| 3 | 3.8 | 85.1 | 7.7 | 7.2 |
| 4 | 11.0 | 13.7 | 36.1 | 50.2 |
| 5 | 10.2 | — | — | — |
| 6 | 14.7 | — | 21.6 | 78.4 |
| 7 | 14.2 | — | — | — |
| 8 | 10.8 | — | 4.0 | 96.0 |
| 9 | 14.0 | — | — | — |
| 10 | 12.3 | — | — | 99.8 |
| 11 | 8.0 | — | — | 100 |

Fractions 6-10 are bulked and the combined fractions are evaluated for their organoleptic properties. The bulked fractions has a complex floral, fruity, honey aroma with a nutty and cinnamic undertone.

FIG. 2 represents the NMR spectrum for the compound having the structure:

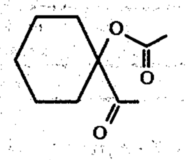

FIG. 3 represents the mass spectrum for the compound having the structure:

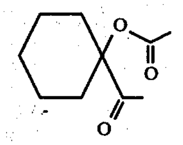

FIG. 4 represents the infrared spectrum for the compound having the structure:

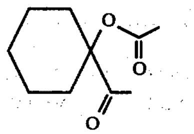

EXAMPLE II

Preparation of 1-Acetyl Cyclohexyl Propionate

Reaction:

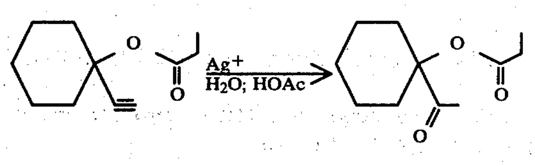

Into a one liter reaction flask, equipped with stirrer, thermometer, heating mantle, reflux condenser and addition funnel is placed 200 grams water and 4 grams of silver nitrate and, in addition, 200 grams propionic acid. The resulting mixture is heated to 75° C. and, while maintaining the temperature of the reaction mass in the range of 75°-80° C. and over a period of 1.5 hours, 1-ethynyl cyclohexyl propionate is (400 grams) is added to the reaction mass. At the end of the addition of the 1-ethynyl cyclohexyl propionate, the temperature of the reaction mass is raised to reflux and heated at reflux (97° C.) for four hours.

The reaction mass is then quenched with 250 ml 20% aqueous sodium chloride solution and the silver chloride is then filtered from the reaction mass.

The organic layer is washed with 500 ml water (one portion) followed by two portions 250 ml saturated sodium bicarbonate and one portion 500 ml saturated sodium chloride solution. The organic layer is then distilled on a "Rushover" column yielding the following fractions:

| Fraction No. | Vapor Temp. | Liquid Temp. | mm. Hg. Pressure | Weight of Fraction |
|---|---|---|---|---|
| 1 | 34/36 | 60/100 | 3 mm | 182 |
| 2 | 57/103 | 90/110 | 3 mm | 140 |

-continued

| Fraction No. | Vapor Temp. | Liquid Temp. | mm. Hg. Pressure | Weight of Fraction |
|---|---|---|---|---|
| 3 | 103 | 189 | 3 mm | 125 |

The material is then redistilled on a fractionation column yielding the following eleven fractions:

| Fraction No. | Vapor Temp. | Liquid Temp. | mm. Hg. Pressure | Weight of Fraction |
|---|---|---|---|---|
| 1 | 41/55 | 90/98 | 3 mm | 27.5 |
| 2 | 56 | 102 | 3 mm | 18.9 |
| 3 | 81 | 104 | 3 mm | 15.5 |
| 4 | 85 | 105 | 3 mm | 26.9 |
| 5 | 85 | 105 | 3 mm | 25.8 |
| 6 | 85 | 105 | 3 mm | 25.4 |
| 7 | 85 | 106 | 3 mm | 22.5 |
| 8 | 85 | 106 | 3 mm | 22.0 |
| 9 | 83 | 107 | 3 mm | 17.0 |
| 10 | 83 | 122 | 3 mm | 20.5 |
| 11 | 81 | 215 | 3 mm | 13.7 |

FIG. 5 represents the GLC profile for the reaction product containing the compound having the structure:

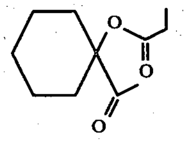

(Conditions: Programmed at 150°-220° C. at 8° C. per minute)

FIG. 6 represents the NMR spectrum for the compound having the structure:

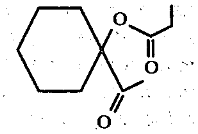

FIG. 7 represents the infrared spectrum for the compound having the structure:

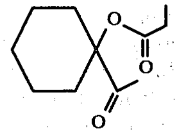

The compound having the structure:

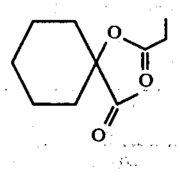

has a rich, fruity (apple) floral (rose) slight green aroma.

EXAMPLE III

Preparation of 1-Acetyl Cyclohexyl Isobutyrate

Reaction:

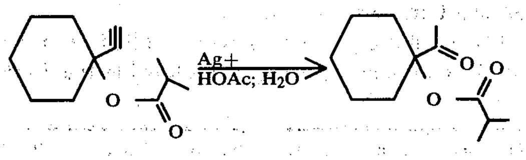

Into a one liter reaction flask equipped with stirrer, thermometer, reflux condenser, addition funnel and heating mantle is placed a mixture of 3.5 grams silver nitrate dissolved in 115 grams of water. 115 Grams of acetic acid is then added to the silver nitrate solution and the resulting mixture is heated to 80° C. The reaction mass is maintained at 80° C. while adding 230 grams of 1-ethynyl cyclohexyl isobutyrate having the structure:

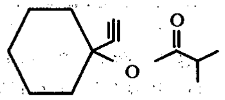

to the reaction mass (230 grams) over a period of 1.75 hours while maintaining the reaction temperature at 80° C. The reaction mass is then maintained with stirring at 80° C. for a period of 5 hours. The reaction mass is then cooled to ambient temperature (25° C.) and quenched with 230 ml 10% hydrochloric acid. The reaction mass is then filtered and the resulting organic layer is washed with 500 ml 10% sodium carbonate solution to a pH of 9 followed by a 500 ml portion of saturated aqueous sodium chloride solution. The resulting product is distilled on a 12" "Rushover" column yielding the following fractions:

| Fraction No. | Vapor Temp. | Liquid Temp. | mm Hg Pressure | Weight of Fraction |
|---|---|---|---|---|
| 1 | 34/27 | 61/100 | 150/145 | 16.4 |
| 2 | 46/82 | 76/97 | 3.0 | 61.0 |
| 3 | 84 | 99 | 3.0 | 42.8 |
| 4 | 85 | 118 | 3.0 | 58.6 |
| 5 | 120 | 214 | 3.0 | 12.6 |

and then fractionally distilled on a 12" Mirror-Goodloe column yielding the following eight fractions:

| Fraction No. | Vapor Temp. | Liquid Temp. | mm Hg Pressure | Reflux Ratio | Wgt. of Fraction |
|---|---|---|---|---|---|
| 1 | 34/57 | 89/96 | 3.0 | 9:1 | 14.4 |
| 2 | 81 | 98 | 3.0 | 9:1 | 17.2 |
| 3 | 85 | 103 | 3.0 | 9:1 | 21.8 |
| 4 | 85 | 103 | 3.0 | 9:1 | 19.2 |
| 5 | 104 | 132 | 3.0 | 9:1 | 23.4 |
| 6 | 104 | 132 | 3.0 | 9:1 | 25.5 |
| 7 | 104 | 132 | 3.0 | 9:1 | 23.4 |
| 8 | 99 | 226 | 3.0 | 9:1 | 14.0 |

The resulting material is trapped out on a GLC column and is ascertained by means of NMR, mass spectral and infrared analyses to have the structure:

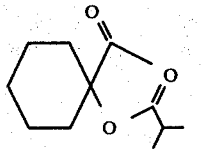

FIG. 8 sets forth the GLC profile for the reaction product of this Example (Conditions: 150°–220° C. at 8° C. per minute on 10% Carbowax column).

FIG. 9 sets forth the NMR spectrum for the compound having the structure:

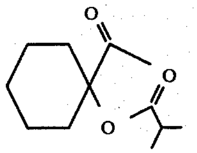

FIG. 10 sets forth the infrared spectrum for the compound having the structure:

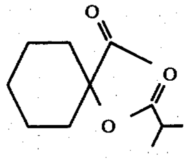

FIG. 11 sets forth the mass spectrum for the compound having the structure:

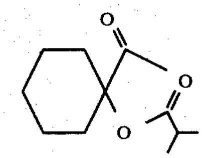

The compound having the structure:

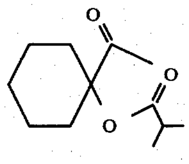

has a green, floral, herbaceous, rather peppery aroma. From a flavor standpoint, it has a sweet, fruity, estery, strawberry-like, ionone-like aroma and flavor characteristic at 5 ppm.

EXAMPLE IV

Floral Perfume Composition

The 1-acetyl cyclohexanyl acetate produced according to Example I has a sweet, fruity, floral odor with figgy, honey notes. This material has great warmth and richness and blends with well with many floral concepts. It is a rather unique floral note of great value to perfumery. Its use may be demonstrated by the following floral fragrance wherein the 1-acetyl cyclohexanyl acetate is used to the extent of 5% by weight.

The 1-acetyl cyclohexanyl propionate produced according to Example II has a similar odor to the acetate but is softer, more floral and slightly less herbaceous. Formula "C" above demonstrates this material in the rose perfume. The addition of 5% by weight of the 1-acetyl cyclohexanyl propionate imparts the floralcy and renders the fragrance more desirable as a perfume.

Both of these products perform quite well in fragrances and are judged to be very valuable fragrance materials:

| FLORAL FRAGRANCE | "A" | "B" | "C" |
|---|---|---|---|
| Citronellol | 12.3 | 12.3 | 12.3 |
| Geraniol | 2.5 | 2.5 | 2.5 |
| Amyl Cinnamic Aldehyde | 24.6 | 24.6 | 24.6 |
| Galaxolide ® 50 (Trademark Tricyclic Isochroman of International Flavors & Fragrances Inc.) | 9.8 | 9.8 | 9.8 |
| Vertenex High Cis (Cis-t-Butylcyclohexenyl Acetate; Para Isomer) | 7.4 | 7.4 | 7.4 |
| Rose Oxide | 0.7 | 0.7 | 0.7 |
| Cinnamic Alcohol | 19.6 | 19.6 | 19.6 |
| Aldehyde C-11 (n-Undecylenic Aldehyde) | 0.5 | 0.5 | 0.5 |
| Aldehyde C-12 (n-Dodecyl Aldehyde in 10% solution in diethyl phthalate) | 0.5 | 0.5 | 0.5 |
| Citronellal (10% solution in diethyl phthalate) | 0.5 | 0.5 | 0.5 |
| Phenyl Ethyl Acetate | 2.5 | 2.5 | 2.5 |
| Ylang Oil | 1.2 | 1.2 | 1.2 |
| Indisan (Hydrogenated derivative of reaction product of Camphene and Resorcinol) | 3.7 | 3.7 | 3.7 |
| Musk Ketone | 5.0 | 5.0 | 5.0 |
| Oakmoss Resin | 0.5 | 0.5 | 0.5 |
| Liatrix Absolute (10% in diethyl phthalate) | 2.5 | 2.5 | 2.5 |
| Vetiver Acetate | 1.2 | 1.2 | 1.2 |
| Diethyl Phthalate | 5.0 | — | — |
| 1-Acetyl Cyclohexanyl Acetate (Produced according to Example I) | — | 5.0 | — |
| 1-Acetyl Cyclohexanyl Propionate (Produced according to Example II) | — | — | 5.0 |

The addition of the 1-acetyl cyclohexanyl acetate to this fragrance improves the odor and the aesthetic character of the perfume rendering it of more value as a perfume. The 1-acetyl cyclohexanyl acetate may be used effectively from a 0.1 up to 25% to give an increased floral, rosey effect with a deep, warm, fruity notes. The fragrance without either of the 1-acetyl cyclohexanyl acetate or the 1-acetyl cyclohexanyl propionate is considered rather thin and less rosey.

EXAMPLE V

Basic Raspberry Flavor Formulation

The following basic raspberry flavor formulation is prepared:

| Ingredients | Parts by Weight |
|---|---|
| Vanillin | 5 |
| Maltol | 5 |
| Parahydroxy Phenyl Butanone | 5 |
| Alpha Ionone (10% in food-grade ethanol) | 2 |
| Ethyl Butyrate | 16 |
| Dimethyl Sulfide | 1 |
| Isobutyl Acetate | 16 |
| Ethyl Acetate | 20 |

-continued

| Ingredients | Parts by Weight |
|---|---|
| Gacial Acetic Acid | 20 |
| Acetaldehyde 100% | 10 |
| Propylene Glycol | 900 |

The basic raspberry formulation is divided into two parts; one part without anything added and the second part with 10% 1-acetyl-cyclohexyl acetate. The flavor is compared at the rate of 100 ppm in water with and without the addition of the 10% 1-acetyl-cyclohexyl acetate. The flavor with the 1-acetyl-cyclohexyl acetate produced according to Example I has a more raspberry juice-like aroma with a fuller, more natural juice-like taste and a better, longer lasting raspberry juice after taste. Therefore a bench panel of experts prefers the flavor with the addition of the 1-acetyl-cyclohexyl acetate.

EXAMPLE VI

A cosmetic soap is prepared according to the procedure set forth in Japanese Pat. No. 79/028-846 published on Sept. 19, 1979 and granted to Kawaken Fine Chemicals Ltd. The soaps are prepared with $RNHCH_2CH(R_1)(0CH_2—CH_2)_n—P(O)(OX)OY$ (wherein R is 16 carbon acyl; $R_1$ is methyl; n is 12; X and Y equals $RNCH_2CH(R_1)(OCH_2CH_2)_n$.

The resulting material is combined with a basic soap material at the rate of 7% and is combined with one of the following materials to provide a cosmetic soap with one of the following aroma profiles:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous, rather peppery aroma.

EXAMPLE VII

A liquid dishwashing detergent with a mild foaming action containing a polyoxyethylene-2-butyl-octyl ether sulphate is prepared according to Japanese Pat. No. 79/028-847 published on Sept. 19, 1979 and assigned to the Kao Soap Company, Ltd.

The liquid detergent contains 17 weight percent of a polyoxyethylene-2-butyl-octyl ether sulphate of the formula: $CH_3(CH_2)_5CH—(C_4H_9)CH_2O(CH_2CH_2O)_n$-$SO_3M$ wherein n is 8 and M is ethanol amine and (b) 14% of an auxiliary active agent which is dimethyl pentyl betaine. To the detergent is added at the rate of 0.2%, 0.3%, 0.4% and 0.8% the following compounds, individually, which yield detergents having the following aroma profiles:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous rather peppery aroma.

EXAMPLE VIII

A low foam detergent containing ethylene oxide/2-butyl-n-octyl alcohol addition compound having the formula:

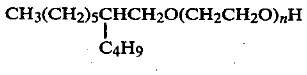

wherein n is 6 is prepared. 1-Acetoxy-2-(2-butenyl) butadiene is first obtained by trimerising butadiene in the presence of a catalyst and acetic acid. The resulting material is hydrolyzed and 7 moles of ethylene oxide is added to the resulting 2-butyl-octyl alcohol to obtain the resulting polyoxyethylene-2-butyl-n-octyl ether. To this material at the rates of 0.2%, 0.3%, 0.5%, 0.7% and 1.5%, the following materials prepared according to Examples I, II or III are added giving rise to a low foam detergent having the following aroma properties:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous rather peppery aroma.

The foregoing detergent is prepared according to Japanese Pat. No. 79/28-848 published on Sept. 19, 1979 and assigned to the Kao Soap Company, Ltd.

EXAMPLE IX

Anionic Builder Free Liquid Detergent Composition Containing Combination of Quaternary Ammonium Cationic Surfactant and Polyethylene Oxide Non-ionic Surfactant A composition containing a cationic surfactant having Formula I and nonionic surfactant of formula $R_3R_4CH—O\ (CH_2CH_2O)_1H$ in the weight ratio of 1:29 respectively and in the total weight amount of (I)+(II)=52%

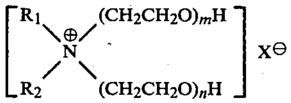

In (I), $R_1$ is ethyl; $R_2$ is 14 carbon alkyl; n+m is 150; n is 80 and m is 70; in (II) $R_3$ and $R_4$ represents $C_{12}$ alkyl.

(I) is obtained by adding ethylene oxide to dodecyl amine and quaternising the resulting dipolyoxyethylenealkylamine with ethyl chloride. (II) is obtained by adding ethylene oxide to isopropyl alcohol.

To the resulting detergent composition 0.1%, 0.2%, 0.5%, 0.7%, 1.0% and 1.5% by weight of the following materials produced according to Examples I, II and III are added giving rise to detergents having the following long lasting aromas:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.

3. 1-acetyl-cyclohexyl isobutyrate produced according to Example III—A green, floral, herbaceous rather peppery aroma.

The foregoing detergent is prepared according to Japanese Pat. No. 79/28-849 published on Sept. 19, 1979 and assigned to the Kao Soap Company, Ltd.

EXAMPLE X

Detergent Formulation

100 Grams of VAROX 188E® (registered trademark of the Sherex Chemical Company, Inc., P.O. Box 646, Dublin, Ohio 43017), a $C_8$–$C_{10}$ alkoxylated $C_8$–$C_{10}$ alkyl ether propyl amine oxide is intimately admixed with 20 grams of stearyl alcohol sulphate. The resulting mixture is intimately admixed with 0.2%, 0.5%, 0.8%, 1.0%, 1.5% and 2.0% concentrations of perfume compositions according to Example IV(B) and Example IV(C). At 5% concentration in water, the resulting detergents all exhibit pleasant soft, floral, herbaceous aromas.

EXAMPLE XI

Perfumed Textile Finish

Hydrophilic polyurethanes for soil-resistant textile finishes are prepared from diisocyanates and compounds containing specific types of reactive hydrogen atoms according to Japanese Pat. No. 79/34-435 published on Oct. 26, 1979 and assigned to the Rhone-Poulenc Industries. These textile finished are pre-fragranced with the perfume compositions of Examples IV(B) and IV(C) as well as with the compounds prepared according to Examples I, II and III.

Thus, a hydrophilic polyurethane is obtained by reaction of 35 weight percent of tolylene diisocyanate; and 65 weight percent of a mixture of 75 weight percent of a compound having the formula $R—(OC_2H_4)_n—OH$ (where R is a 15 carbon hydrocarbon residue and n is such as the molecular weight is 6,500 and 25 weight percent of 1,4-butylene diol; and 1% by weight of a nitrogen containing compound with the formula $R_1NX_1X_2$ where $R_1$ is $C_5$ alkyl and $X_1$ and $X_2$ represent aminopentyl. The tertiary nitrogen atom compound $R_1—NX_1X_2$ is quaternised with the diisocyanate after the reaction and the ratio of isocyanate to total mobile hydrogens is 1.0.

The resulting material is then intimately admixed with compounds produced according to Example I, II or III at the levels of 0.5%, 1.0%, 1.5%, 2.0% and 4.0% giving rise to textile finishes which when coated on to textiles during washing or finishing yield the following aroma profiles:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous rather peppery aroma.

When, instead of the compounds produced according to Examples I, II or III, perfume compositions produced according to Example IV(B) or IV(C) are added to the textile finishes produced above at levels of 1.0%, 1.5%, 2.0% and 5.0%, the textile finishes when applied to clothing during washing or finishing yield pleasant floral/herbaceous aromas which are long lasting subsequent to the washing or finishing cycle.

EXAMPLE XII

Perfumed and Sized Textiles Using Perfumed Water-Soluble Polyurethanes

Water-soluble polyurethanes for the sizing of textiles derived from anionic sulphonated polyesters are produced containing varying quantities of perfume compositions produced according to Example IV(B) and IV(C) and compounds produced according to Example I, II or III, according to Japanese Pat. No. 79/34-436 published on Oct. 26, 1979 assigned to the Rhone-Poulenc Industries.

Specifically, the water-soluble polyurethanes are prepared by reacting (A) an anionic sulphonated polyester having an average molecular weight of 2200, acid value 15 mg KOH/gram and S content 0.9 weight percent with (B) tolylene diisocyanate at a temperature of 185° C. and a mole ratio of isocyanate:hydroxide plus carboxylic acid of 1.5. To the resulting compound at levels of 0.5%, 1.0%, 1.5%, 2.0%, 2.5%, 4.0% and 5.0% are added compounds produced according to Examples I, II and III giving rise to the following aromas:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous rather peppery aroma.

In place of the compounds produced according to Examples I, II and III, perfumes produced according to Example IV(C) and IV(B) are added yielding sizings having pleasant floral/herbaceous aromas. When the sizings are added to the synthetic yarns, the yarns have a faint, pleasant floral/herbaceous aroma which is long lasting.

EXAMPLE XIII

Perfumed Penetration Agents

Perfumed penetration agents containing hydroxyalkyl amino sulphonic acid is prepared according to Japanese Pat. No. 79/34711 published on Oct. 29, 1979 and assigned to the Asahi Denka Kogyo Corporation. These penetration agents contain the compounds of Examples I, II or III or the perfume compositions of Example IV(B) or IV(C).

Thus, the penetration agent contains the compound $R_1CH(OH)CH_2N[(CH_2)_nSO_3M]CH_2CH(OH)R_2$ (where each represent n-octyl and M represents potassium; and n represents 3 and pentylbenzenesulphonic acid sodium salt. The ratio of the alkylbenzenesulphonate and the compound having the structure $R_1CH(OH)CH_2N[(CH_2)_nSO_3M]—CH_2CH(OH)R_2$ is 1:1 (mole ratio). To the resulting composition is added at levels of 0.5%, 1.0%, 1.5%, 2.0%, 2.5%, 3.0% and 4.0%, the compounds produced according to Examples I, II and III giving rise to the following aromas:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.

2. 1-acetyl-cyclohexyl isobutyrate produced according to Example III—A green, floral, herbaceous rather peppery aroma.

In place of the compounds produced according to Examples I, II and III are added at the above levels perfume compositions prepared according to Example IV(B) or IV(C) giving rise to a pleasant herbaceous/floral aromas.

EXAMPLE XIV

Perfumed Acrylic Polymer Lattices Used in the Manufacture of Binders, Carpet Backings and Paper and Textile Dressings Acrylic polymer latices which are perfumed combining low solids content with high viscosity without the use of thickening agents are prepared according to Japanese Pat. No. 79/34-798 published on Oct. 29, 1979 and assigned to the B.F. Goodrich Company. Specifically, a thickenable polymer latex is obtained by first emulsion-copolymerising 52% by weight of methyl methacrylate with 3.2% by weight of glycidyl acrylate until about 50% of the polymers have been polymerised; and finally graft-polymerising in the presence of 0.3% of methylacrylic acid the remainder of the material which theretofore has been unpolymerised. The latex is thickened by addition of $NH_3$ (aqueous). To the latex is added at the rate of 2%, 4%, 6% and 8% compounds prepared according to Examples I, II or III yielding the following aromas (and masking the "chemical" aroma particularly after utilization thereof for carpet backing and textile dressings:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
2. 1-acetyl-cyclohexyl isobutyrate produced according to Example III—A green, floral, herbaceous rather peppery aroma.

EXAMPLE XV

Perfumed Fabric Whiteners

Azastilbene fluorescent whiteners which are perfumed are prepared by reacting aldehydes with dialkyl (substituted pyridinyl) methyl phosphonates and have the structure:

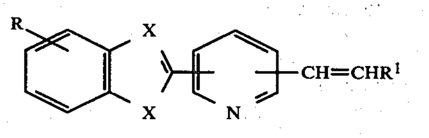

wherein X is oxygen; R is chloro; and R' is phenyl. The preparation is according to Japanese Pat. No. 79/34-780 published on Oct. 29, 1979 and assigned to the Mitsui Toatsu Chemical Inc. To this whitener is added at the levels of 0.05%, 0.1%, 0.15%, 0.2%, 0.3% and 0.5%. Compounds prepared according to Examples I, II and II. The whiteners have imparted thereto aromas as indicated in the following Table:

1. 1-acetyl-cyclohexyl acetate produced according to Example I—A sweet, fruity, floral, honey-like aroma with figgy and rose nuances.
2. 1-acetyl-cyclohexyl propionate produced according to Example II—A rich, fruity (apple), floral (rose), slightly green aroma.
3. 1-acetyl-cyclohexyl isobutyrate produced according to Example III—A green, floral, herbaceous rather peppery aroma.

When these fabric whiteners are used in conjunction with detergents in cleansing fabrics, the resulting fabrics do not retain any "chemical" aroma and thus "deodorized" and, instead, have faint pleasant floral/herbaceous aromas on drying after the washing cycle.

EXAMPLE XVI

Raspberry Flavor

The following mixture is prepared:

| Ingredient | Parts by Weight |
|---|---|
| Para-hydroxy benzyl acetone | 5 |
| Vanillin | 2 |
| Maltol | 3 |
| Alpha-ione (1% solution in propylene glycol) | 15 |
| Isobutyl acetate | 15 |
| Ethyl butyrate | 5 |
| Ethyl acetate | 5 |
| Dimethyl sulfide (10% solution in propylene glycol) | 5 |
| Acetic acid | 15 |
| Acetaldehyde | 20 |
| Propylene glycol | 910 |

1-Acetyl-cyclohexyl isobutyrate prepared according to Example III is added to the above mixture at rates of 0.02%, 0.04%, 0.06%, 0.1% and 0.15%. Flavor formulations with this derivative are then compared with a flavor formulation without the ester at the rate of 0.01% in water (100 parts per million) by a bench panel. The flavor formulation containing the ester has a strong delicate raspberry aroma with strawberry nuances which characteristics are not reproduced by the flavor formulation which does not contain the said ester derivative.

EXAMPLE XVII

The following mixture is prepared:

| Ingredients | Parts by Weight |
|---|---|
| Natural Raspberry Concentrate Juice | 2½% |
| Water | 85% |
| Sugar syrup (37½° Baume) | 12½% |

The natural juice-like taste of this raspberry juice is imparted in increased strength by addition of either of the following materials at the rate of from 0.02 ppm up to 1.0 ppm:

(a) 1-acetyl-cyclohexeyl acetate produced according to Example I;

(b) 1-acetyl-cyclohexyl isobutyrate prepared according to Example III;

(c) A 50:50 weight:weight mixture of 1-acetyl-cyclohexyl isobutyrate prepared according to Example III and 1-acetyl-cyclohexyl acetate prepared according to Example I

EXAMPLE XVIII

Flavor Formulation

The following mixture is prepared:

| Ingredients | Parts by Weight |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |

1-Acetyl-cyclohexyl acetate produced according to Example I was added to 975 grams of the above mixture which was then called "Test Composition". A control composition was prepared by adding 25 grams of additional lemon oil to 975 grams of the above mixture.

The test and control compositions were added to the food products described hereinafter and the proportions shown for 100 kilograms of material to be flavored:

| | |
|---|---|
| Cake | 20 grams |
| Pudding | 5-10 grams |
| Cooked sugar | 15-20 grams |

Cooked sugar—100 ml of sugar syrup (prepared by dissolving 1 kilogram of sucrose in 600 ml of water) and 20 grams of glucose were mixed together and slowly heated to 145° C. The flavor was added and the mass allowed to cool and harden.

Pudding—To 500 ml of warmed milk were added with stirring a mixture of 60 grams sucrose and 3 grams of pectin. The mixture was boiled for a few seconds and the flavor was added. The mixture was allowed to cool.

Cake—The following ingredients were mixed together:

| | |
|---|---|
| Vegetable margarine | 100 grams |
| Sodium chloride | 1.5 grams |
| Sucrose | 100 grams |
| Eggs | 2 |
| Flour | 100 grams |

The flavor was added and the mass was cooked for 40 minutes at 180° C. The finished foodstuff samples were tested by a panel of trained persons who had to express their views about the flavor of the samples. All members of the panel declared with no hesitation that the test samples had a more distinguished fruity and woody note than the control samples and at the same time a red-berry character.

EXAMPLE XIX

A. Powder Flavor Composition

20 Grams of the flavor composition of Example V is emulsified in a solution containing 300 grams gum acacia and 70 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
|---|---|
| Liquid raspberry flavor composition of Example V | 20 |
| Propylene glycol | 9 |
| Cab-O-Sil ® M-5 (Brand of Silica produced by the Cabot Corporation of 125 High Street, Boston, Mass. 02110; Physical Properties: Surface area: $200m^2/gm$ Nominal particle size: 0.012 microns Density: 2.3 lbs/cu.ft.) | 5.00 |

The Cab-O-Sil is dispersed in the raspberry flavor composition of Example V with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XX

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example V is added to the solution which is then homogenized to form an emulsion having particle size typically in the range of 2-5 microns. This material is kept at 120° F. under which conditions the gelatin will not jell.

Coacervation is induced by adding, slowly and uniformly 40 parts by weight of a 20% aqueous solution of sodium sulphate. During coascervation the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XXI

Chewing Gum

100 Parts by weight of chicle are mixed with 4 parts by weight of the flavor prepared in accordance with Example XIX. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XXII

Chewing Gum

100 Parts by weight of chicle are mixed with 18 parts by weight of the flavor prepared in accordance with Example XIX. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting raspberry flavor.

EXAMPLE XXIII

Toothpaste Formulation

The following separate groups of ingredients are prepared:

| PARTS BY WEIGHT | INGREDIENTS |
|---|---|
| Group "A" | |
| 30.200 | Glycerine |
| 15.325 | Distilled water |
| .100 | Sodium benzoate |
| .125 | Saccharin sodium |
| .400 | Stannous fluoride |
| Groups "B" | |
| 12.500 | Calcium carbonate |
| 37.200 | Dicalcium phosphate (Dihydrate) |
| Group "C" | |
| 2.000 | Sodium N—Lauroyl Sarcosinate (foaming agent) |
| Group "D" | |
| 1.200 | Flavor Material of Example XIX |
| 100.000 (TOTAL) | |

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1–1.5 minutes).

EXAMPLE XXIV

Chewable Vitamin Tablets

The flavor material produced according to the process of Example XIX is added to a Chewable Vitamin Tablet Formulation at a rate of 10 gm/Kg which chewable vitamin tablet formulation is prepared as follows:

In a Hobart Mixer, the following materials are blended to homogeneity:

| Ingredients | Gms/100 Tablets |
|---|---|
| Vitamin C (ascorbic acid) as ascorbic acid-sodium mixture 1:1 | 70.00 |
| Vitamin $B_1$ (thiamine mononitrate) as Rocoat ® 200 thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XIX | (as indicated above) |
| Certified lake color | 5.0 |
| Sweetener-sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant long-lasting, consistently strong raspberry flavor for a period of 12 minutes.

EXAMPLE XXV

Tobacco Formulation

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of the 1-acetyl-cyclohexyl acetate produced according to Example I. The control cigarettes not containing the 1-acetyl-cyclohexyl acetate produced according to Example I and the experimental cigarettes which contain the 1-acetyl-cyclohexyl acetate produced according to the process of Example I are evaluated by paired comparison and the results are as follows:

The experimental cigarettes are found to have a sweet, minty, cooling, spicey, anisic, berry-like aroma and taste prior to and on smoking in the main stream and the side stream and to be sweeter and more aromatic. All cigarettes are evaluated for smoke flavor with a 20 mm cellulose acetate filter.

When used in the filter rather than on the tobacco the cigarettes having in the filter the 1-acetyl-cyclohexyl acetate produced according to Example I have a sweet, minty, cooling, spicey, anisic and berry-like flavor and taste prior to and on smoking.

EXAMPLE XXVI

Tobacco Formulation

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of the 1-acetyl-cyclohexyl propionate produced according to Example II. The control cigarettes not containing the 1-acetyl-cyclohexyl propionate produced according to Example II and the experimental cigarettes which contain the 1-acetyl-cyclohexyl propionate produced according to the process of Example II are evaluated by paired comparison and the results are as follows:

The experimental cigarettes are found to have a sweet, fruity, pineapple-like and woody aroma and taste prior to and on smoking in the main stream and the side stream and to be sweeter and more aromatic. All cigarettes are evaluated for smoke flavor with a 20 mm cellulose acetate filter.

When used in the filter rather than on the tobacco the cigarettes having in the filter the 1-acetyl-cyclohexyl propionate produced according to Example II have a sweet, fruity, pineapple-like and woody flavor and taste prior to and on smoking.

EXAMPLE XXVII

Tobacco Formulation

A tobacco mixture is prepared by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of 1-acetyl-cyclohexyl isobutyrate produced according to Example III. The control cigarettes not containing the 1-acetyl-cyclohexyl isobutyrate produced according to Example III and the experimental cigarettes which contain the 1-acetyl-cyclohexyl isobutyrate produced according to the process of Example III are evaluated by paired comparison and the results are as follows:

The experimental cigarettes are found to have a sweet, green, pepper, dill-like, natural spice, cuban tobacco-like aroma and taste prior to and on smoking in the main stream and the side stream and to be sweeter and more aromatic. All cigarettes are evaluated for smoke flavor with a 20 mm cellulose acetate filter.

When used in the filter rather than on the tobacco the cigarettes having in the filter the 1-acetyl-cyclohexyl isobutyrate produced according to Example III have a sweet, green, pepper, dill-like, natural spice, cuban tobacco-like flavor and taste prior to and on smoking.

EXAMPLE XXVIII

Preparation of 1-Acetyl-3,3,5-Trimethyl-Cyclohexanol Acetate

EXAMPLE XXVIII(A)

Reduction of Isophorone

Reaction:

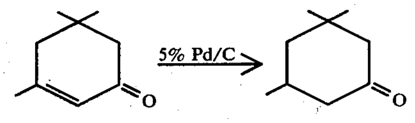

Into a Parr shaker flask attached to a Parr shaker is placed 40 ml ethyl alcohol, 5.5 grams of 5% palladium-on-carbon catalyst and 275 grams of isophorone. Hydrogen is added after the pressure flask is closed up to 50 psig. The hydrogen is pumped in until no more hydrogen is taken up.

After 115 psi of hydrogen is taken up, the Parr shaker flask contents are filtered, the solvent is stripped and the reaction mass is used in Example XXVIII(B).

EXAMPLE XXVIII(B)

Addition of Acetylene to Hydrogenated Isophorone

Reaction:

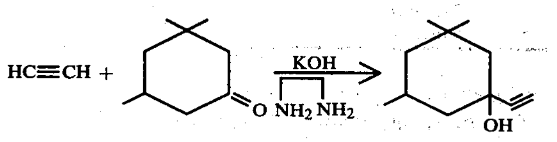

Into a two liter reaction flask equipped with stirrer, isopropanol/dry ice bath, two glass "Y" tubes, thermometer, and condenser, addition funnel and acetylene entrance tube, nitrogen purge and bubbler is placed 17 grams of potassium hydroxide flakes and 830 ml of ethylene diamine. The resulting mixture is stirred and cooled to about 15° C. using a cooling bath.

Over a period of thirty minutes, acetylene is added to the reaction mass while maintaining the reaction mass at 10°-20° C. As the acetylene addition is continued, the hydrogenated isophorone derivative produced according to Example XXVIII(A) is added slowly. Both rates of addition, the acetylene and hydrogenated isophorone are adjusted to maintain saturation with acetylene. The over-all addition takes four hours. The reaction mass is maintained at 10°-20° C. during the simultaneous addition of the ketone and the acetylene.

After the ketone addition is complete, the acetylene feed is continued for another two hours. GLC analysis indicates no further change.

The reaction mass is then transferred to a separatory funnel and an equal amount of an ice/water slurry is added slowly to the reaction mass. The aqueous phase is then extracted with three 250 ml volumes of diethyl ether. The organic layers are recombined and washed with two volumes of water followed by two volumes of 5% hydrochloric acid to neutrality. The resulting product is then dried over anhydrous magnesium sulfate, filtered and concentrated. The crude product weighing 437.2 grams is fractionated on a 1' silver column and fractions 15-22 are bulked.

EXAMPLE XXVIII(C)

Acetylation of Reaction Product of Example XXVIII(B)

Reaction:

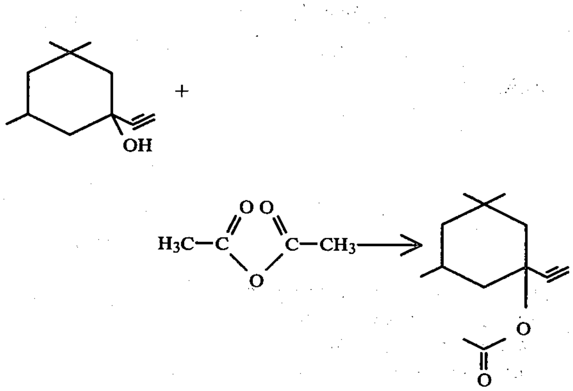

Into a 100 ml reaction flask equipped with magnetic stir, thermometer, condenser, addition funnel and heating mantle are placed 30 ml acetic anhydride and 5 drops of phosphoric acid. The reaction mixture is heated to 75°-80° C. and addition of the product of Example XXVIII(B) is started while maintaining the reaction mass at 75°-80° C. Over a period of 0.75 hours, 20 grams of the reaction product of Example XXVIII(B) is added to the reaction mass (until no further change in the GLC profile observed).

The reaction mixture is then transferred to a separatory funnel and an equal amount of water is added.

The organic and aqueous layers resulting are separated and the aqueous layer is extracted with 3 volumes of toluene. The organic layers are then combined and washed with two volumes of water followed by two volumes of 10% sodium carbonate solution. The resulting material is then dried over anhydrous magnesium sulphate and the solvent is evaporated on a rotary evaporator yielding 30.1 grams of crude product. The resulting material is fractionated on a micro Vigreux column and fractions 4-10 are bulked for use in Example XXVIII(D).

EXAMPLE XXVIII(D)

Hydration Reaction to Yield 1-Acetyl-3,3,5-Trimethyl Cyclohexanol Acetate

Reaction:

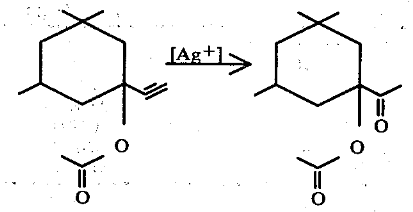

Into a 50 ml reaction flask equipped with addition funnel, thermometer, magnetic stir, condenser, heating mantle, and thermowatch is placed 8 ml water, 8 ml concentrated acetic acid and 0.2 grams of silver nitrate. The resulting mixture is heated to 80° C. and over a period of three hours while maintaining the reaction mass at 80° C., the reaction product of Example XXVIII(C) having the structure:

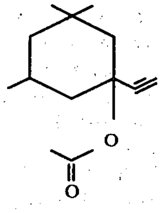

is added to the reaction mass.

The reaction mass is then quenched with an equal amount of saturated sodium chloride solution to yield a precipitate including, interalia, silver chloride.

The organic and aqueous phases are separated and the organic phase is washed with two volumes of water; two volumes of saturated sodium carbonate; and finally with two volumes of saturated sodium chloride solution.

The resulting product is dried over anhydrous magnesium sulphate and the solvent is evaporated on a rotary evaporator yielding 9.5 grams of crude product.

The resulting product is distilled yielding the following fractions:

| Fraction No. | Vapor Temp. | Liquid Temp. | mm Hg Pressure | Weight of Fraction |
|---|---|---|---|---|
| 1 | 47/67 | 79/84 | 0.5 | 0.4 |
| 2 | 76 | 88 | 0.5 | 0.3 |
| 3 | 75 | 88 | 0.5 | 0.8 |
| 4 | 80 | 95 | 0.5 | 0.7 |
| 5 | 78 | 90 | 0.5 | 1.4 |
| 6 | 78 | 90 | 0.5 | 1.3 |
| 7 | 60 | 125 | 0.5 | 1.5 |

The distillation takes place on a micro-Vigreux column from a 25 ml flask.

The resulting product, bulked fractions 4–7, has a sweet, floral, minty, camphoraceous, honey, green, fruity, orris, leathery and earthy aroma profile with a strong tobacco undertone from a fragrance standpoint.

At 10 ppm, its taste includes a floral and green aroma with an earthy, green, bitter and astringent flavor profile.

The resulting compound prior to and on smoking in both the main stream and the side stream has a sweet, fruity, berry-like, woody and slightly green organoleptic profile in smoking articles.

EXAMPLE XXIX

Floral Perfume Formulation

The following floral fragrance formulation is prepared:

| Ingredients | Parts by Weight |
|---|---|
| Citronellol | 12.3 |
| Geraniol | 2.5 |
| Amyl Cinnamic Aldehyde | 24.6 |
| Galaxolide® 50 (Trademark Tricyclic Isochroman of International Flavors & Fragrances Inc.) | 9.8 |
| Vertenex High Cis (Cis-t-Butylcyclohexenyl Acetate; Para Isomer) | 7.4 |
| Rose Oxide | 0.7 |
| Cinnamic Alcohol | 19.6 |
| Aldehyde C-11 (n-Undecylenic Aldehyde) | 0.5 |
| Aldehyde C-12 (n-Dodecyl | 0.5 |

-continued

| Ingredients | Parts by Weight |
|---|---|
| Aldehyde in 10% solution in diethyl phthalate) | |
| Citronellal (10% solution in diethyl phthalate) | 0.5 |
| Phenyl Ethyl Acetate | 2.5 |
| Ylang Oil | 1.2 |
| Indisan (Hydrogenated derivative of reaction product of Camphene and Resorcinol) | 3.7 |
| Musk Ketone | 5.0 |
| Oakmoss Resin | 0.5 |
| Liatrix Absolute (10% in diethyl phthalate) | 2.5 |
| Vetiver Acetate | 1.2 |
| 1-Acetyl-3,3,5-trimethyl cyclohexanol acetate produced according to Example XXVIII(D) | 6.0 |

The 1-acetyl-3,3,5-trimethyl cyclohexanol acetate produced according to Example XXVIII(D) imparts a sweet, floral, minty, camphoraceous, honey-like, green, fruity, orris, leathery and earthy aroma profile to the floral fragrance and causes it to have an intense tobacco-like undertone.

What is claimed is:

1. A process for augmenting or enhancing the organoleptic properties of a consumable material selected from the group consisting of perfume compositions, and colognes, comprising the step of adding to said consumable material an organoleptic property augmenting or enhancing quantity of at least one compound having the generic structure:

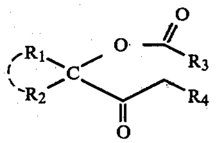

wherein $R_1$ and $R_2$ taken together complete a cycloalkyl moiety or a methyl, dimethyl or trimethyl cycloalkyl moiety containing five or six carbon atoms in the ring and wherein R3 is $C_1$–$C_3$ lower alkyl and $R_4$ is methyl or hydrogen.

2. The process of claim 1 wherein the consumable material is a perfume composition.

* * * * *